United States Patent [19]

Ishikawa et al.

[11] Patent Number: 5,728,130
[45] Date of Patent: Mar. 17, 1998

[54] ULTRASONIC TROCAR SYSTEM

[75] Inventors: Manabu Ishikawa, Hachioji; Masakazu Gotanda; Tomohisa Sakurai, both of Sagamihara; Yoshitaka Honda, Tokorozawa, all of Japan

[73] Assignee: Olympus Optical Co., Ltd., Tokyo, Japan

[21] Appl. No.: 786,221

[22] Filed: Jan. 21, 1997

[30] Foreign Application Priority Data

| Mar. 22, 1996 | [JP] | Japan | 8-066763 |
| May 20, 1996 | [JP] | Japan | 8-124665 |
| Jul. 29, 1996 | [JP] | Japan | 8-199178 |
| Jul. 29, 1996 | [JP] | Japan | 8-199185 |

[51] Int. Cl.$^6$ .......... A61B 17/34; A61B 17/20; A61M 5/00
[52] U.S. Cl. .......... 606/185; 604/22; 604/264
[58] Field of Search .......... 604/19, 22, 164, 604/264; 606/1, 108, 127, 128, 167, 169, 170, 171, 184, 185

[56] References Cited

U.S. PATENT DOCUMENTS 5,449,370  9/1995  Vaitekunas .
5,472,447  12/1995  Abrams et al. .

FOREIGN PATENT DOCUMENTS 5-57863  8/1993  Japan .

Primary Examiner—Glenn K. Dawson
Attorney, Agent, or Firm—Armstrong, Westerman, Hattori, McLeland & Naughton

[57] ABSTRACT

An ultrasonic trocar system includes a cannula having a guide bore, an obturator to be passed through the guide bore of the cannula so that the obturator can be removed, and a vibration generator for generating ultrasonic vibrations to be propagated to the obturator. The obturator is vibrated at an ultrasonic frequency to puncture a somatic layer. An intermediate member is interposed between the cannula and obturator.

21 Claims, 31 Drawing Sheets

FIG.19
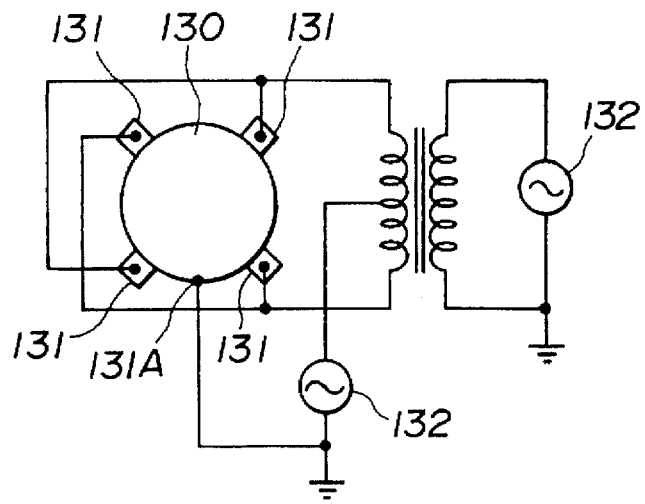
FIG.20
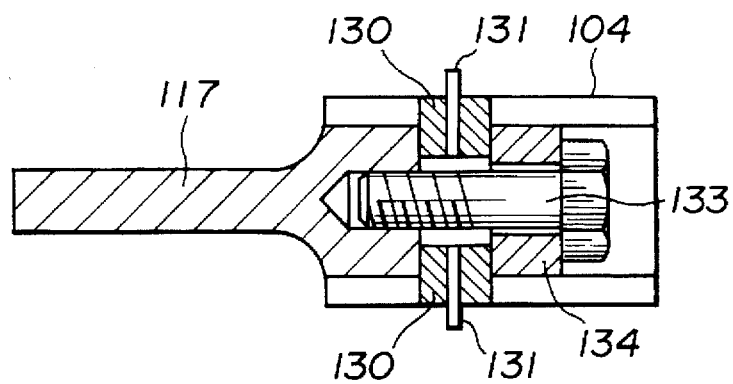
FIG.21
DISTRIBUTION OF DISPLACEMENTS IN FLEXURAL VIBRATION
FIG.22
DISTRIBUTION OF DISPLACEMENTS IN AXIAL-DIRECTION VIBRATION
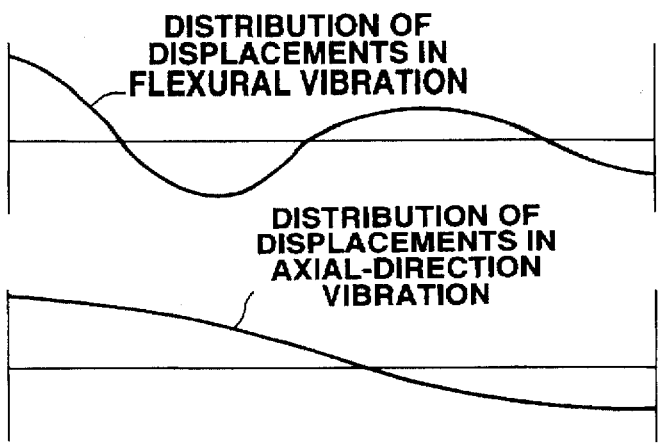

ULTRASONIC TROCAR SYSTEM

BACKGROUND OF THE INVENTION

1. Field of the Invention

The present invention relates to an ultrasonic trocar system for using ultrasonic vibrations to puncture a somatic layer and to guide introduction of a medical appliance into a body cavity.

2. Description of the Related Art

In recent years, less-invasive surgery utilizing an endoscope has been adopted as a surgical procedure to be substituted for laparotomy. This surgery has the advantage of hardly affecting a patient and allowing the patient to leave a hospital shortly.

In less-invasive surgery, a trocar is used as a guide member for guiding an appliance such as an endoscope or therapeutic instrument to the inside of a body. The trocar is composed of a cannula that is a hollow member having a guide bore, and an obturator to be inserted through the guide bore of the cannula so that the obturator can be removed.

For introducing a medical appliance into the abdominal cavity using such a trocar, for example, a gas is injected into the abdominal cavity in order to dilate the abdominal cavity. Alternatively, the abdominal wall is lifted up in order to reserve a cave serving as a treatment work space. Thereafter, with the obturator inserted through the guide bore of the cannula of the trocar, the tip of the obturator jutting out from the distal end of the cannula is advanced to pierce the abdominal wall. In other words, while the abdominal wall is being incised by the trocar, the trocar is introduced into the abdominal cavity (cave). Once the trocar including the cannula has been inserted, the obturator is removed with the cannula alone left in the abdominal wall. A medical appliance such as an endoscope or therapeutic instrument is passed through the guide bore of the cannula, whereby the medical appliance is introduced into an intended region within the body cavity through the guide bore. Observation or surgery is then carried out.

For puncturing the patient's abdominal wall using this kind of trocar while incising the abdominal wall, a considerable amount of puncturing force is needed. An operator is requested to carry out such manipulation as pressing the trocar against the patient's abdominal wall forcibly. However, a force for thrusting the trocar must be adjusted properly. This poses a problem that it is hard to control the extent of the force. Specifically, if a force to be applied is too feeble, the trocar cannot be thrust. On the contrary, if the force is excessive, there is the fear of damaging an organ within the abdominal cavity.

In the past, improvements have been made for reducing an amount of force used to thrust a trocar into the abdominal wall: the tip of an obturator is sharpened to the greatest extent; a blade is attached to the tip; or the shape of the tip is devised. Moreover, the tip of the obturator may be sheathed in order not to damage an internal organ after the tip of the trocar penetrates through the abdominal cavity.

Recently, an ultrasonic trocar intended to improve the ability of a trocar to puncture a tissue by transmitting ultrasonic vibrations to an obturator so as to vibrate the obturator has been proposed as another means for reducing an amount of puncturing force in, for example, U.S. Pat. No. 5,449,370. Using the trocar utilizing ultrasonic vibrations, the trocar can be thrust into the abdominal wall easily with little expertise while sufficient safety is ensured.

In the case of the foregoing ultrasonic trocar, there is no problem as long as a cannula has a relatively small diameter of 3 mm or 5 mm. If the cannula has a relatively large diameter equal to or larger than 10 mm, a drawback occurs. That is to say, if the diameter of a trocar is large, the diameter of an obturator is also large, and therefore the area of a portion of the tip of the obturator in direct contact with a living tissue becomes large. If the obturator vibrating at an ultrasonic frequency is in contact with the living tissue with a certain pressure or greater for a prolonged period of time, there is the fear that the living tissue may be thermally burnt because of heat stemming from ultrasonic vibrations or frictional heat occurring between the living tissue and obturator due to ultrasonic vibrations. The larger the contact area of the obturator is, the larger the area of a thermal burn is.

OBJECTS AND SUMMARY OF THE INVENTION

An object of the present invention is to provide an ultrasonic trocar system offering the improved ability of a trocar to puncture a tissue and suppressing occurrence of a thermal burn in a punctured region.

Another object of the present invention is to provide an ultrasonic trocar system capable of readily thrusting even a large-diameter trocar and suppressing occurrence of a thermal burn.

Yet another object of the present invention is to provide an ultrasonic trocar system in which an intermediate member adaptable to a plurality of kinds of cannulas having different diameters is included in order to improve a puncturing ability and suppress occurrence of a thermal burn in a punctured region, and one kind of obturator can be used in combination with the cannulas having different diameters, and which offers improved maneuverability and reduced cost of the whole system.

One constitution of the present invention is an ultrasonic trocar system comprising: a cannula having a guide bore; an obturator to be inserted through the guide bore of the cannula so that it can be removed; and a vibration generating means for generating ultrasonic vibrations to be propagated to the obturator. The obturator is vibrated at an ultrasonic frequency to puncture a somatic layer. An intermediate member is interposed between the cannula and obturator.

Another constitution of the present invention is an ultrasonic trocar system comprising: an obturator to be vibrated at an ultrasonic frequency for puncturing a somatic layer; a plurality of kinds of cannulas having different diameters and having guide bores into which the obturator can be inserted; and a plurality of kinds of intermediate members, interposed between said cannulas and obturator, having inner diameters matching the outer diameter of the obturator and outer diameters matching the different inner diameters of the cannulas.

Other features and advantages of the present invention will be fully apparent from the description below.

BRIEF DESCRIPTION OF THE DRAWINGS

FIG. 19 is a circuit diagram showing a circuit for vibrating a flexural transducer;

FIG. 20 is a sectional view showing an example of the inner structure of a handpiece having the flexural transducer;

FIG. 21 is a waveform chart illustrating the distribution of displacements in a flexural vibration occurring in the structure shown in FIG. 20;

FIG. 22 is a waveform chart illustrating the distribution of displacements in an axial-direction vibration occurring in the structure shown in FIG. 20;

FIG. 36A is a side view, and FIG. 36B is a view from a tip;

FIG. 37A is a side view, and FIG. 37B is a view from a tip;

DESCRIPTION OF THE PREFERRED EMBODIMENTS

Figure 1:
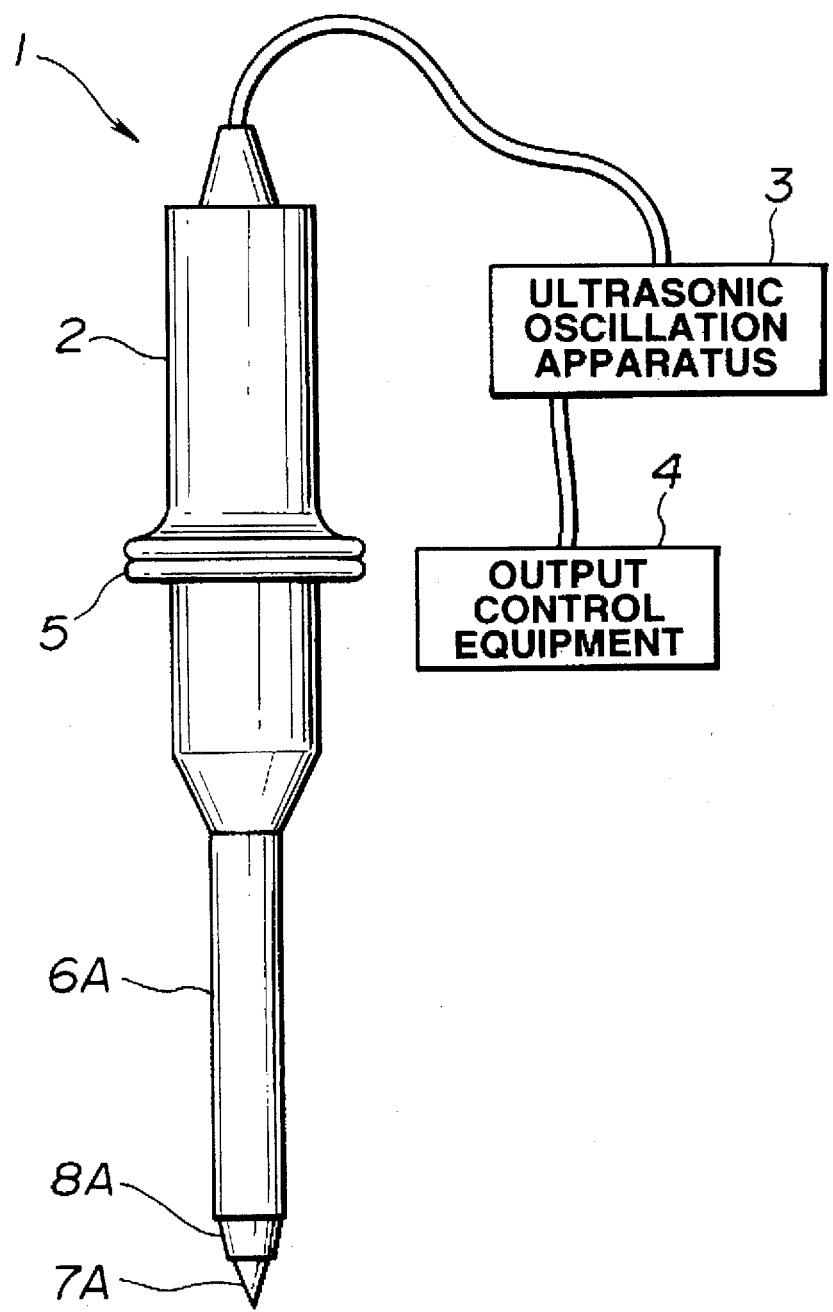
FIG. 1 is a schematic view showing the overall configuration of an ultrasonic trocar system in accordance with the first embodiment of the present invention.

FIGS. 1 to 4 shows the first embodiment of the present invention. FIG. 1 shows the overall configuration of an ultrasonic trocar system in accordance with the first embodiment.

The ultrasonic trocar system of this embodiment comprises an ultrasonic trocar 1, an ultrasonic oscillation apparatus 3, and an output control equipment 4. The ultrasonic trocar 1 comprises a handpiece 2, a hollow cannula 6A coupled to the distal end of the handpiece 2 by a joint member 5, an obturator 7A inserted through the cannula and screwed to the handpiece, and a hollow tapered member 8A that is an intermediate member capable of being inserted between the cannula 6A and obturator 7A.

The ultrasonic oscillation apparatus 3 supplies energy required for ultrasonic vibrations to the handpiece 3. The output control equipment 4 is formed with a foot switch for controlling the output of energy.

A means for coupling the handpiece 2 with the cannula 6A is not limited to the foregoing joint member 5. The handpiece 2 and cannula 6A may not be coupled to each other but may be separated from each other.

Figure 2:
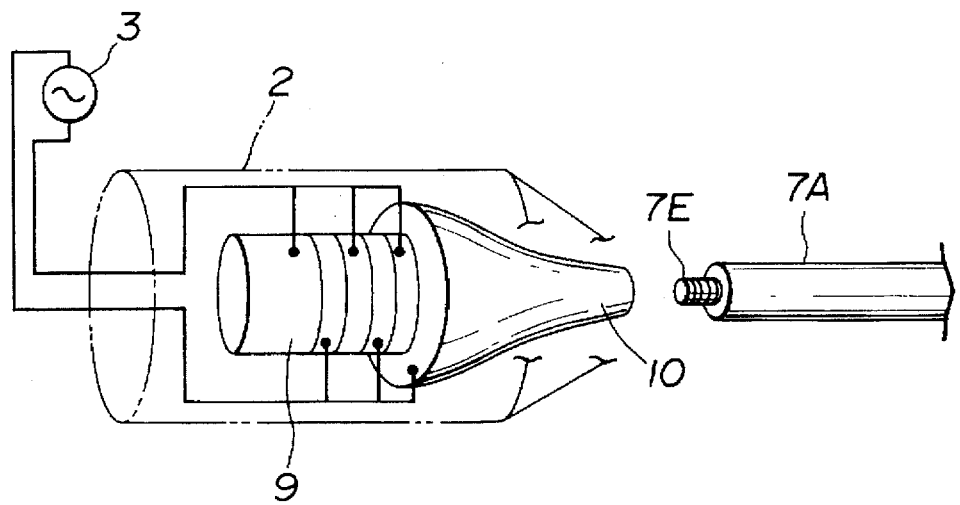
FIG. 2 is a schematic view showing the inner structure of a handpiece forming the proximal part of an ultrasonic trocar in the first embodiment.

FIG. 2 is a diagram showing the internal structure of the handpiece 2 forming the proximal part of the ultrasonic trocar 1. The handpiece 2 includes an ultrasonic transducer 9 on the proximal side thereof, and a horn 10 for enlarging the amplitude of ultrasonic vibrations generated by the ultrasonic transducer 9. The ultrasonic transducer 9 includes bipolar voltage input electrodes and is designed to convert energy supplied from the ultrasonic oscillation unit 3 to ultrasonic oscillations.

The distal end of the horn 10 is female-threaded so that it can be screwed tightly to the obturator 7A. By contrast, the proximal end of the obturator 7A has a male thread 7E formed. Owing to this structure, if the obturator 7A is broken, the obturator 7A alone can be replaced with a new one but the handpiece 2 need not be replaced with a new one. This is economic.

The ultrasonic transducer 9 is not limited to the one composed of bipolar voltage input electrodes but may be of an electrostriction or magnetostriction type.

Figure 3:
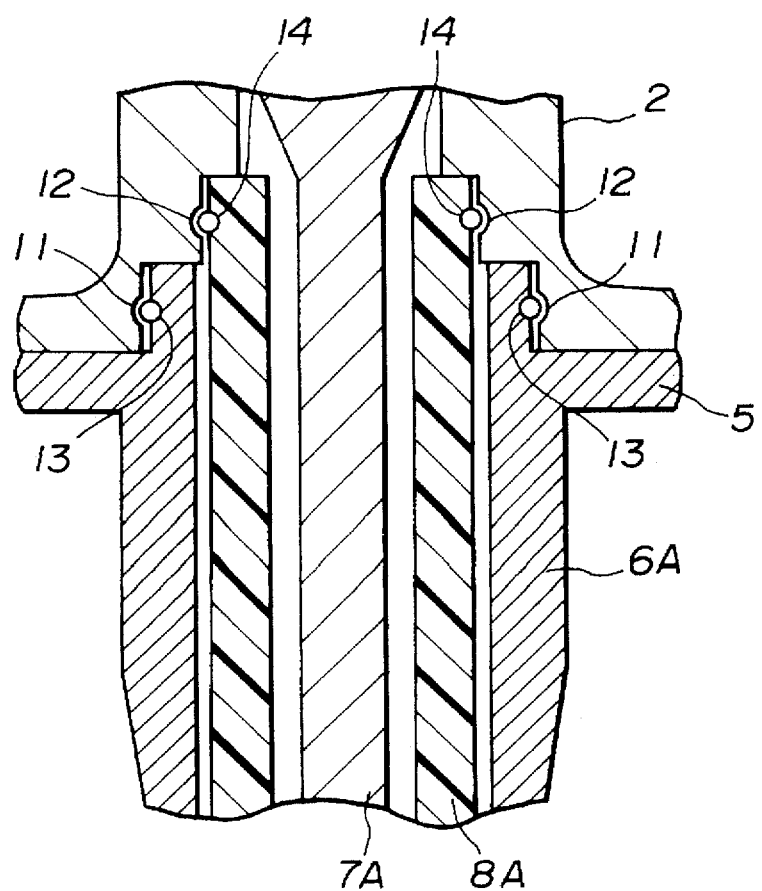
FIG. 3 is a sectional view of the handpiece, cannula, tapered member, and obturator constituting the central part of the ultrasonic trocar in the first embodiment.

FIG. 3 is a sectional view of the handpiece 2, cannula 6A, tapered member 8A, and obturator 7A constituting the central part of the ultrasonic trocar 1. The handpiece 2 has two grooves 11 and 12 formed at the distal end thereof. The cannula 6A has an O ring 13 fixed to the proximal end thereof. The O ring 13 is fitted into the groove 11, whereby the cannula 6A can be attached to the handpiece 2. Moreover, the tapered member 8A has an O ring 14 fixed to the proximal end thereof. The O ring 14 is fitted into the groove 12, whereby the tapered member 8A can be attached to the handpiece 2.

The cannula 6A is made of a material such as plastic, a metal, or polytetrafluoroethylene (PTFE), and is a hollow member having an outer diameter of 10 mm or larger. The tapered member 8A is a hollow member formed with a member having a slide-enabling property made of PTFE or the like. A gap is created between the Cannula 6A and tapered member 8A.

The obturator 7A is a solid-core member made of a material such as a titanium alloy or aluminum alloy. There is a gap between the tapered member 8A and obturator 7A. Owing to the gap, even when the obturator 7A is vibrated at an ultrasonic frequency, the ultrasonic vibrations will not propagate to the tapered member 8A.

Figure 4:
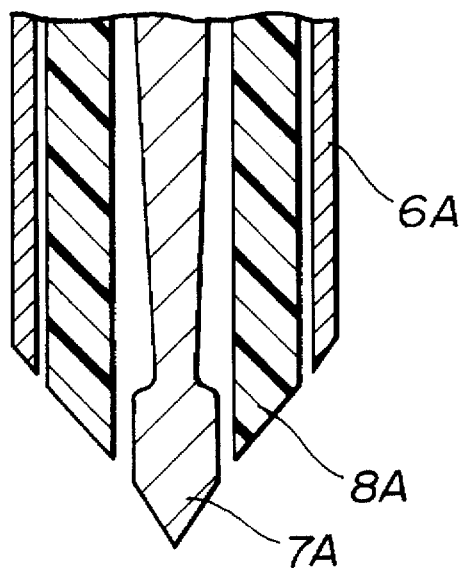
FIG. 4 is a sectional view of the cannula, tapered member, and obturator constituting the distal part of the ultrasonic trocar in the first embodiment.

FIG. 4 shows the structure of the distal part of the ultrasonic trocar 1, and is a sectional view of the cannula 6A, tapered member 8A, and obturator 7A. The tip of the cannula 6A, the distal end of the tapered member 8A, and the distal blade of the obturator 7A are shaped at an acute angle so that the slopes thereof can be continuous. This enables puncture of the wall of an abdominal cavity.

The tapered member 8A should be structured not to receive ultrasonic vibrations from the obturator 7A and not to propagate ultrasonic vibrations to the cannula 6A. For example, the tapered member 8A is made of a material having a different acoustic impedance from the obturator 7A and cannula 6A. In addition, preferably, the surface of the tapered member 8A is formed with a member having an excellent slide-enabling property. For improving the slide-enabling property of the surface, as mentioned above, a material having an excellent slide-enabling property such as PTFE is used or the surface is smoothened. This results in a desired effect. More preferably, the tapered member 8A is made of a material having low thermal conductivity that is so low as not to conduct heat stemming from the tip of the obturator 7A.

In this embodiment, a gap is reserved between the obturator 7A and tapered member 8A or between the cannula 6A and tapered member 8A in order to separate the respective members. The present invention is not limited to this structure. Alternatively, the respective members may be in contact with one another as long as they are acoustically separated from one another so that vibrations originating from the obturator 7A can neither propagate nor be interrupted.

Next, the operations of the ultrasonic trocar system having the aforesaid configuration will be described.

First, the tapered member 8A and cannula 6A are attached to the handpiece 2 so that the O rings 13 and 14 can be fitted into the grooves 11 and 12. A small site above the wall of an abdominal cavity to be punctured by the obturator 7A is incised using a knife or the like. Thereafter, the tip of the obturator 7A is abutted on the incised site, and the output control equipment 4 such as a foot switch is switched ON.

Energy is then transmitted from the ultrasonic oscillation apparatus 3 to the ultrasonic transducer 9 in the handpiece 2, whereby ultrasonic vibrations occur. The generated ultrasonic vibrations has the amplitude thereof enlarged by the horn 10, and is then propagated to the tip of the obturator 7A. With the propagated ultrasonic vibrations, the tip of the obturator 7A is gradually thrust into the wall of the abdominal cavity through the incised site. Thereafter, the incised site is further pressed wide by the distal end of the tapered member 8A. Finally, even the outer circumference of the cannula 6A can be readily thrust into the wall of the abdominal cavity.

The tip of the obturator 7A vibrates at an ultrasonic frequency. However, since there is the gap between the obturator 7A and tapered member 8A, the ultrasonic vibrations will not propagate to the tapered member 8A and cannula 6A. In such a usage that the obturator 7A is thrust obliquely into the wall of an abdominal cavity, ultrasonic vibrations made by the obturator 7A may presumably propagate to the tapered member 8A. However, since the tapered member 8A is formed with a member having an excellent slide-enabling property made of PTFE or the like, the ultrasonic vibrations will not propagate to the tapered member 8A and cannula 6A.

As mentioned above, the tapered member 8A does not vibrate at an ultrasonic frequency. However, since the distal end of the tapered member 8A is shaped at an acute angle so that the slope thereof can be continuous to that of the tip of the obturator 7A, even the outer circumference of the cannula 6A can be readily thrust into the wall of the abdominal cavity.

As described above, according to the first embodiment, even when the ultrasonic trocar 1 having a relatively large diameter of 10 mm or larger is thrust into the wall of an abdominal cavity, since the obturator 7A has the same size as the one used in conjunction with an ultrasonic trocar having a relatively small diameter of 3 mm or 5 mm, there is not the concern that the area of a thermal burn on the wall of the abdominal cavity caused by ultrasonic vibrations gets larger. Moreover, since the distal end of the tapered member 8A and the tip of the obturator 7A are each shaped to have a continuous sharp slope, even if the obturator 7A alone vibrates at an ultrasonic frequency, the ultrasonic trocar 1 can readily be thrust into the wall of the abdominal cavity.

Figure 5:
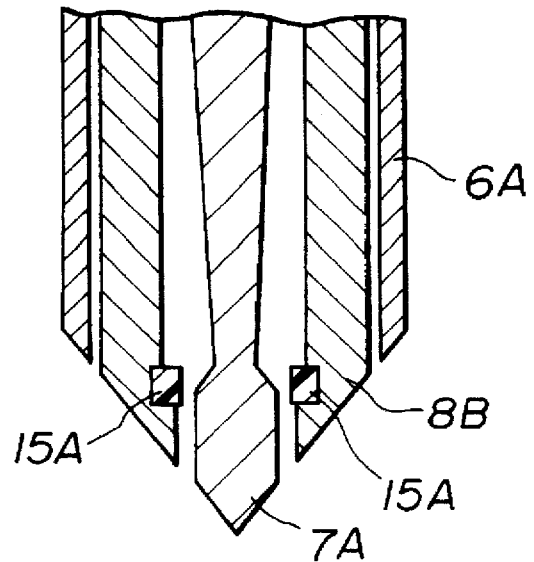
FIG. 5 is a sectional view showing the structure of the distal part of an ultrasonic trocar of an ultrasonic trocar system in accordance with the second embodiment of the present invention.

FIG. 5 is a sectional view of the distal part of an ultrasonic trocar of an ultrasonic trocar system in accordance with the second embodiment of the present invention. Component members identical or similar to those of the first embodiment will be assigned the same reference numerals. The description of the members will be omitted.

A tapered member 8B has almost the same structure as the tapered member 8A in the first embodiment. Only a difference from the tapered member 8A lies in a point that a slide-enabling member 15A formed with a PTFE member shaped like a C ring is located on the inner circumference of the distal part thereof. In this case, the tapered member 8B may be formed with a member having a slide-enabling property made such as a PTFE member as described in the first embodiment, but is not limited to this member. The material of the tapered member 8B may be a metal or plastic.

Owing to the foregoing structure, the ultrasonic trocar in this embodiment is used in the same manner as that in the first embodiment.

Thus, according to the second embodiment, not only the same advantage as that provided by the first embodiment is exerted but also since the slide-enabling member 15A such as a PTFE member is located on the distal part of the tapered member 8B, in whatever manner the ultrasonic trocar 1 is used, ultrasonic vibrations will not propagate to the tapered member 8B and cannula 6A. Moreover, since it will not take place that the obturator 7A comes into direct contact with and rubs against the tapered member 8B, frictional heat, powder, or sound does not occur. Even if the tapered member 8B is not formed with a member having a slide-enabling property such as a PTFE member which has been mentioned in the first embodiment, the same advantage as that of the first embodiment can be exerted.

Figure 6:
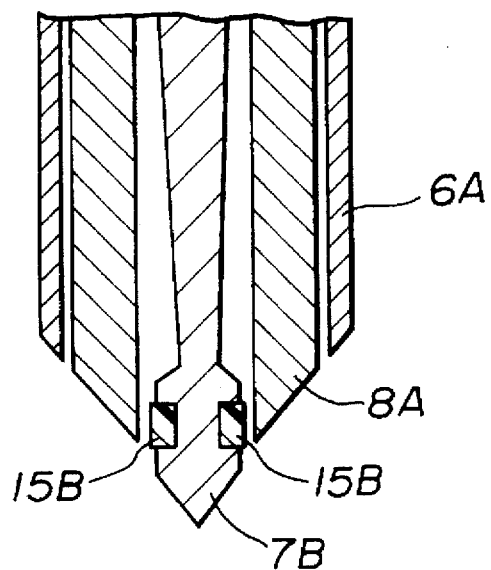
FIG. 6 is a sectional view showing the structure of the distal part of an ultrasonic trocar of an ultrasonic trocar system in accordance with the third embodiment of the present invention.

FIG. 6 is a sectional view of the distal part of an ultrasonic trocar of an ultrasonic trocar system in accordance with the third embodiment of the present invention. Component members identical or similar to those of the first embodiment will be assigned the same reference numerals. The description of the members will be omitted.

An obturator 7B has almost the same structure as the obturator 7A of the first embodiment. Only a difference from the obturator 7A lies in a point that a slide-enabling member 15B such as a PTFE member shaped like a C ring is affixed to the outer circumference of the distal part of the obturator 7B or engaged therewith so that the member can be disengaged from it. In this case, the material of the tapered member 8A may be, as described in the first embodiment, PTFE but is not limited to PTFE. The material of the tapered member 8A may be a metal or plastic.

With the above structure, the ultrasonic trocar 1 of this embodiment is used in the same manner as that of the first embodiment.

According to the third embodiment, the same advantage as that of the first embodiment can be provided. Moreover, since the slide-enabling member 15B such as a PTFE member is located on the distal part of the obturator 7B, in whatever manner the ultrasonic trocar 1 is used, ultrasonic vibrations will not propagate to the tapered member 8A and cannula 6A. Furthermore, since it will not take place that the obturator 7B comes into direct contact with and rubs against the tapered member 8B, frictional heat, powder, or sound does not occur. The tapered member 8A may not therefore be a member having a slide-enabling property such as a PTFE member as described in the first embodiment, but the same advantage as that of the first embodiment can still be exerted.

Moreover, since the slide-enabling member 15B is replaceable, if the slide-enabling member 15B is deformed thermally during the use of the ultrasonic trocar 1, the slide-enabling member 15B can be replaced with a new one, and thus the ultrasonic trocar 1 becomes reusable. Moreover, when cleaning is needed, since the slide-enabling member 15B can be disengaged and cleaned, cleaning efficiency improves.

Figure 7:
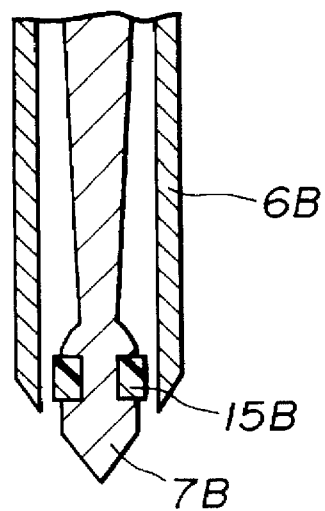
FIG. 7 is a sectional view showing an example of the structure of an obturator of the ultrasonic trocar of the third embodiment to be inserted into a cannula having a relatively small diameter for use.

By the way, since the obturator 7B in this embodiment has the slide-enabling member 15B, as shown in FIG. 7, unless the tapered member 8A is used, the obturator 7B can be inserted to a cannula 6B having a relatively small diameter of 5 mm for practical use. Moreover, as mentioned above, a cannula to be used in combination with the obturator is not limited to the cannula 6 of 5 mm in diameter. Even if a cannula to be employed has any other diameter, as long as a tapered member contoured like the cannula is available, the same obturator 7B can be used and the same operation and advantage as those of the third embodiment can be exerted.

For example, when two or more kinds of cannulas are used during surgery, as long as one handpiece and obturator are available, a tapered member having a different diameter is fitted to a cannula to be employed. Thus, a desired cannula can be thrust into a somatic layer. Owing to this structure, it becomes possible to improve the maneuverability of an ultrasonic trocar and reduce the cost of a whole system.

Figure 8:
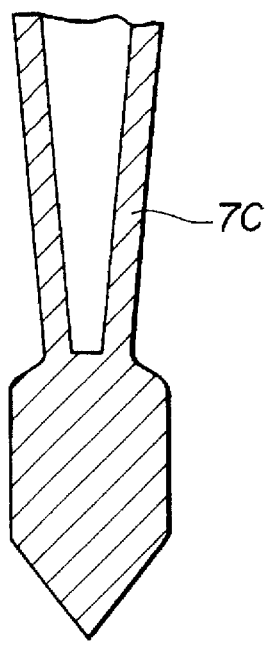
FIG. 8 is a sectional view showing the first variant of the distal part of the obturator.
Figure 9:
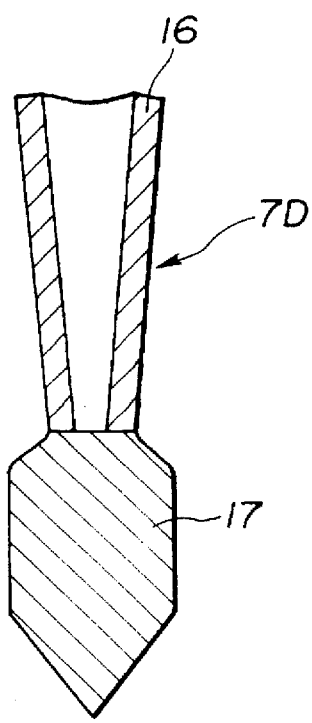
FIG. 9 is a sectional view showing the second variant of the distal part of the obturator.

FIGS. 8 and 9 are sectional views of variants of the obturators 7A and 7B described in the first to third embodiments.

An obturator 7C of the first variant shown in FIG. 8 is made of a material such as a titanium alloy or aluminum alloy and formed in one united body to be hollow. An obturator 7D of the second variant shown in FIG. 9 is made of a material such as a titanium alloy or aluminum alloy and completed by welding a solid-core distal part 17 made also of a titanium alloy or aluminum alloy into the distal end of a hollow body 16.

Needless to say, the obturators 7C and 7D shown in FIG. 8 and 9 may, like the obturator 7B, be provided with a slide-enabling member 15B such as a PTFE member. Moreover, something that is lighter than the member forming the obturator 7C or 7D, or water or any other thing having a different acoustic impedance may be put in the hollow of the obturator 7C or 7D.

As mentioned above, since an obturator lighter than either of the solid-core obturators 7A and 7B is employed, the obturator itself can be prevented from heating. Consequently, occurrence of a thermal burn on the wall of an abdominal cavity can be suppressed more effectively.

Figure 10:
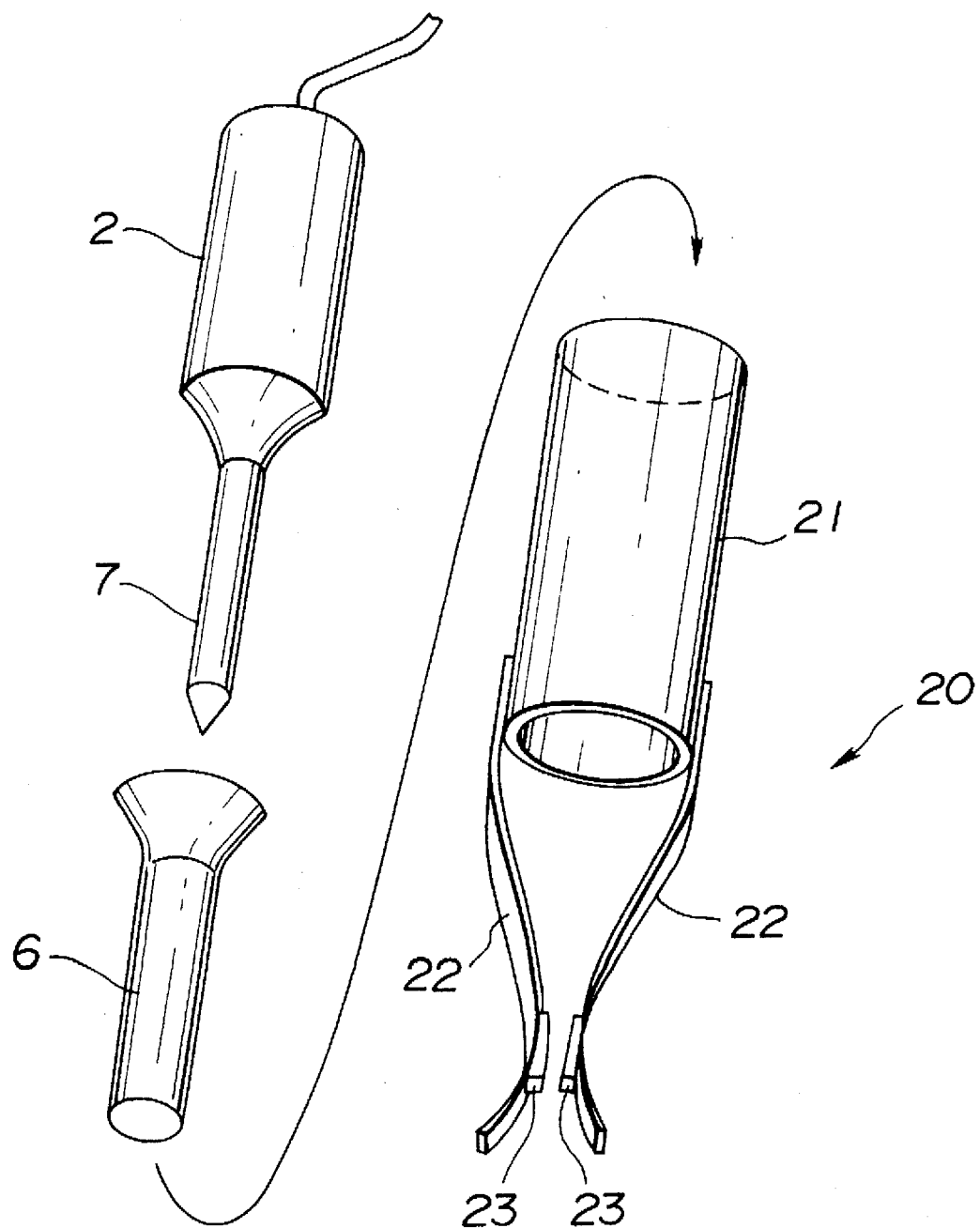
FIG. 10 is a schematic view showing the first example of the structure of an opener closer that is an auxiliary tool used to puncture a somatic layer with the handpiece and cannula of the ultrasonic trocar.

FIG. 10 is a schematic view showing the handpiece 2 and cannula 6A or 6B (hereinafter, cannula 6) as well as the first example of the structure of an opener closer that is an auxiliary tool for use in puncturing the wall of a body cavity.

An opener closer 20 is composed broadly of a cylindrical body 21 into which the cannula 6 can be inserted, and an opening aid 22 linked to the distal part of the body 21. The opening aid 22 is composed of two blade springs. The spacing between the two blade springs gets smaller as it goes from the proximal end to distal end, and the tips of the blade springs are slightly widened. A anti-contact tool 23 that is a slide-enabling member such as a PTFE member is attached to each of parts of the two blade springs that are mutually approaching to the greatest extent. The anti-contact tool 23 is intended to prevent contact between the opening aid 22 and obturator 7A, 7B, 7C, or 7D (hereinafter, obturator 7).

Next, an operation of thrusting the obturator 7 into the wall of a body cavity with the help of the opener closer 20 will be described. First, a knife is used to incise a small site at a position through which the obturator 7 is thrust into the wall of a body cavity. With the distal part of the opener closer 20 inserted to the incised site, the obturator 7 and cannula 6 are inserted through a proximal aperture of the body 21 and pushed toward the distal end thereof. The pushing force causes the opening aide 22 to open outward, whereby the incised site is extended forcibly. The tip of the obturator 7 is then introduced into the body cavity through the incised site. Using this kind of opener closer 20, an ultrasonic trocar can readily be thrust into a tissue.

Figure 11:
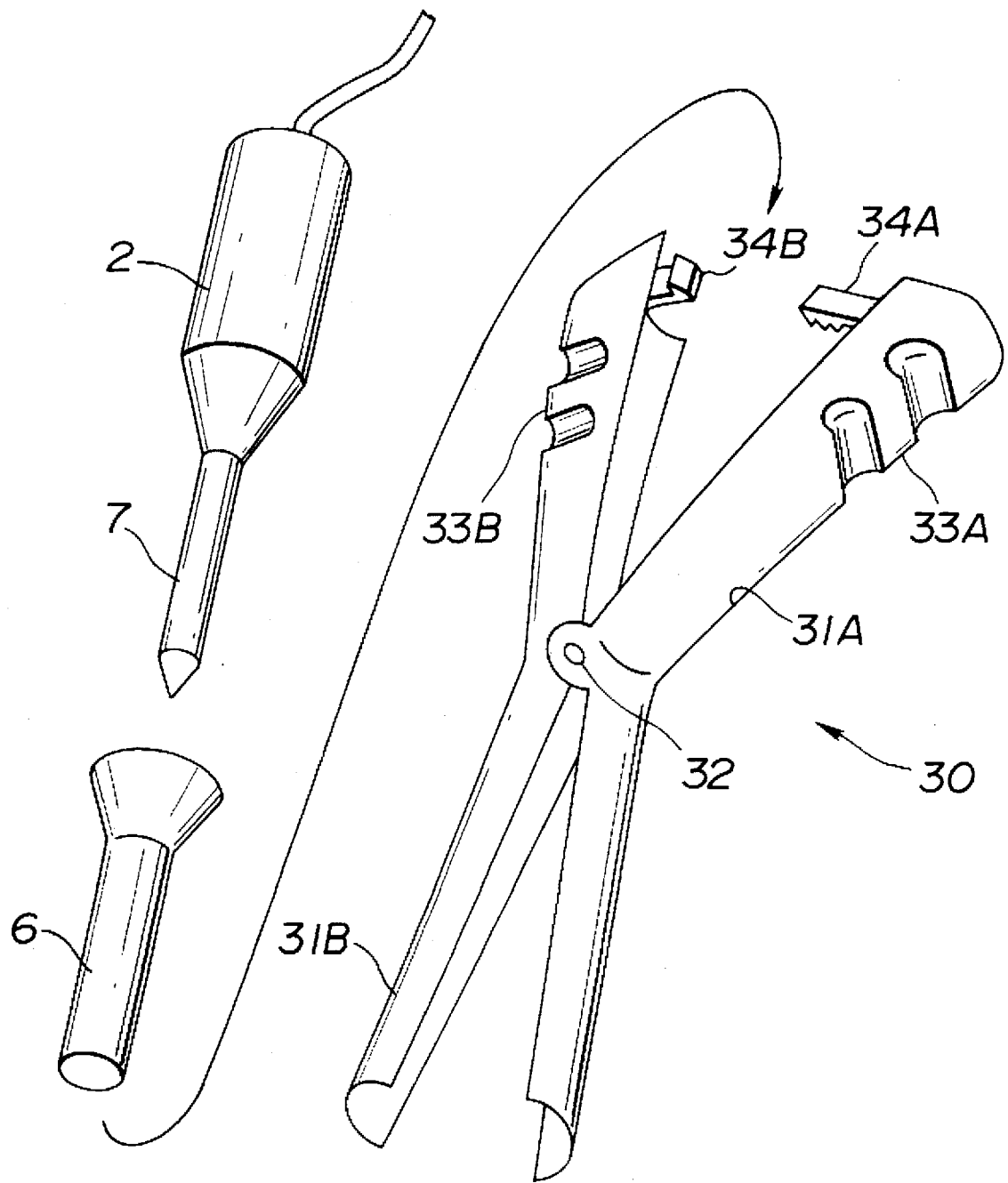
FIG. 11 is a schematic view showing the second example of the structure of an opener closer that is an auxiliary tool used to puncture a somatic layer with the handpiece and cannula of the ultrasonic trocar.

FIG. 11 is a schematic view showing the second example of the structure of an opener closer different from that shown in FIG. 10. An opener closer 30 is composed broadly of bodies 31A and 31B. The bodies 31A and 31B are each shaped like a semi-cylindrical letter L (elbow). Bents 32 of the elbow-like bodies are joined with each other so that the bodies can pivot freely. A spring that is not shown is attached to the inside of the joined bents 32. In a normal state, the elastic force of the spring keeps the proximal ends of the bodies 31A and 31B apart. Grip sections 33A and 33B are formed on the proximal parts of the bodies 31A and 31B respectively. A wheel 34A and pawl 34B formed at the proximal ends of the bodies 31A and 31B constitute a ratchet. When the proximal ends of the bodies 31A and 31B are met, they are held in that state.

Next, an operation of thrusting the obturator 7 into the wall of a body cavity with the help of the opener closer 30 will be described. First, a knife or the like is used to incise a small site at a position through whichthe obturator 7 is thrust into the wall of a body cavity. With the distal parts of the bodies 31A and 31B inserted into the incised site, the obturator 7 and cannula 6 are inserted through the proximal ends of the bodies 31A and 31B and pushed toward the distal ends thereof. Meanwhile, the grip sections 33A and 33B are grabbed and met with each other. This causes the distal ends of the bodies 31A and 31B to part outward, whereby the incised site is extended forcibly. Consequently, the tip of the obturator 7 is introduced into the body cavity through the incised site.

Thus, the employment of the opener closer 30 makes it possible to thrust an ultrasonic trocar into a tissue readily.

Figure 12:
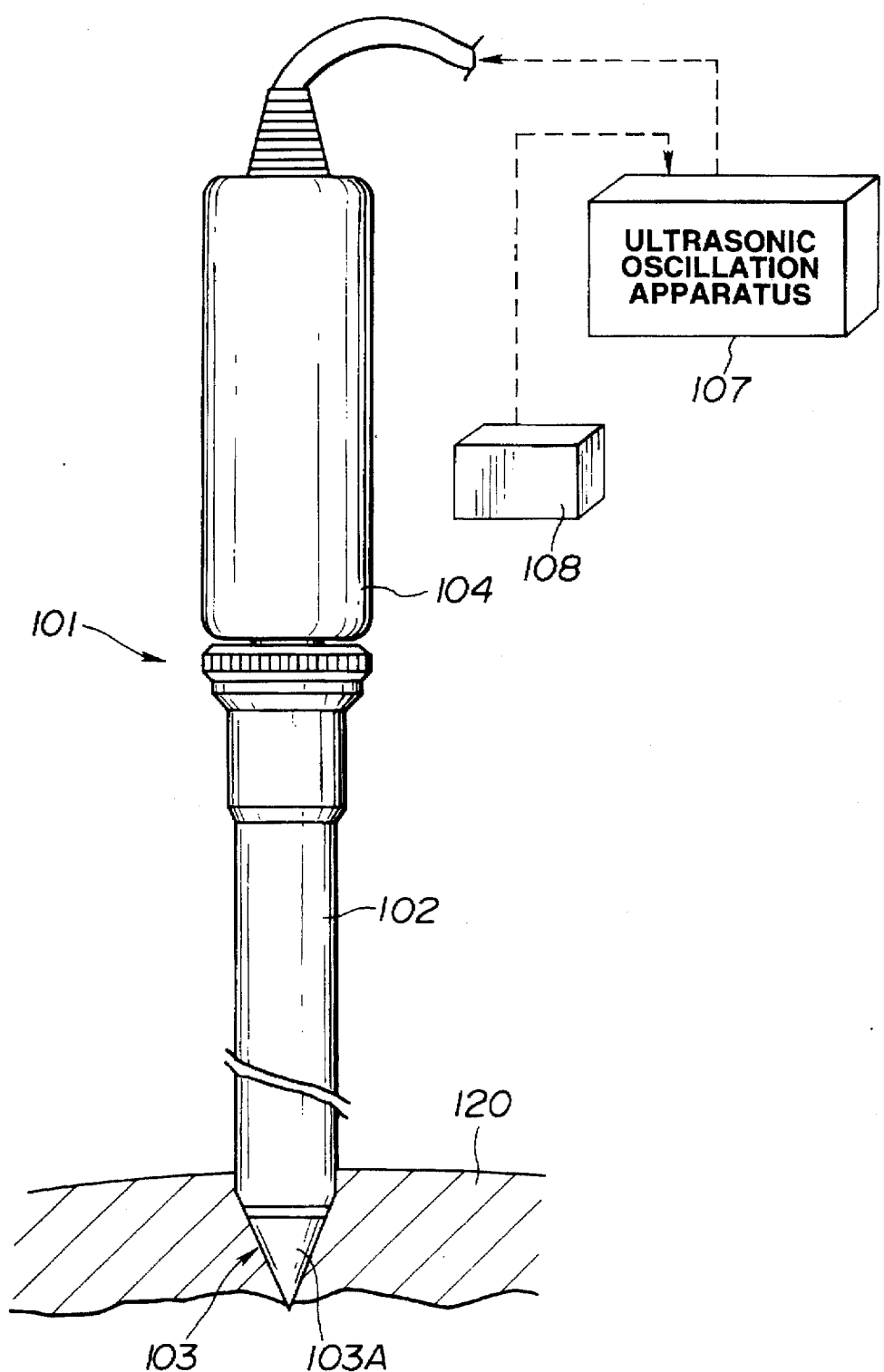
FIG. 12 is a schematic view showing the appearance of an ultrasonic trocar system in accordance with the fourth embodiment of the present invention.
Figure 13:
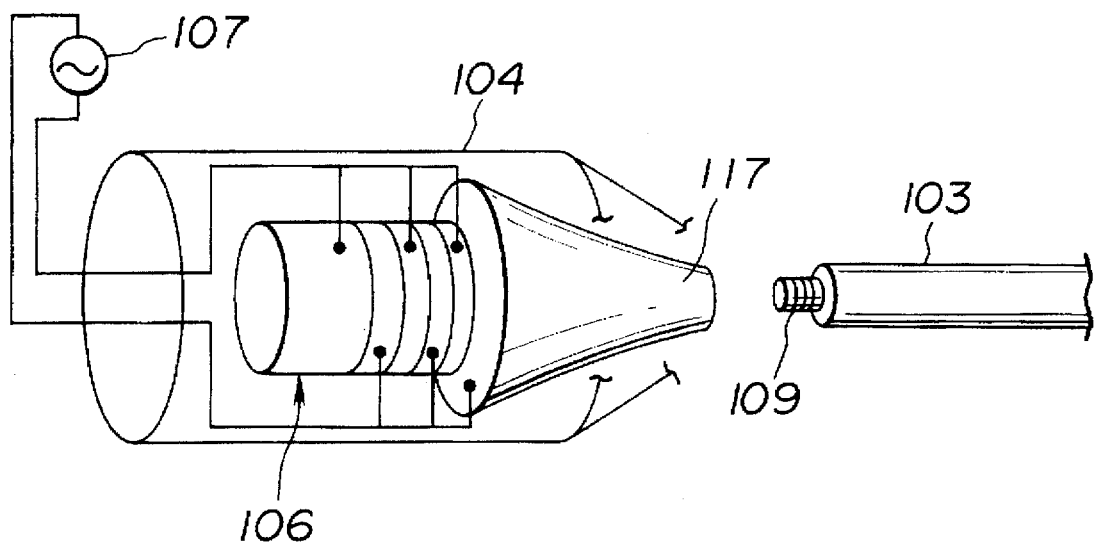
FIG. 13 is a schematic view showing the structure of an ultrasound generator in an ultrasonic trocar of an ultrasonic trocar system in accordance with the fourth embodiment.
Figure 14:
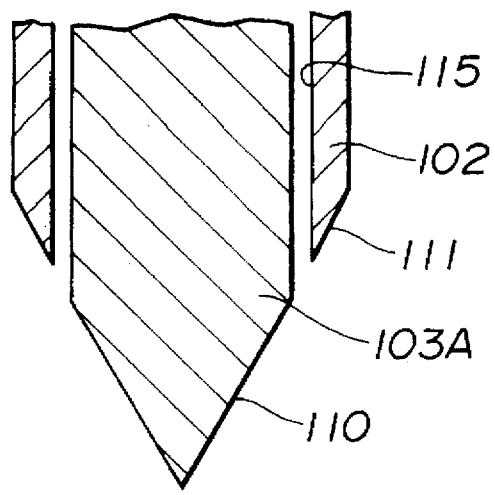
FIG. 14 is a sectional view showing the structure of the distal part of the ultrasonic trocar in the fourth embodiment.

FIGS. 12 to 14 show the fourth embodiment of the present invention. Referring to FIG. 12, an ultrasonic trocar 101 in this embodiment comprises a cannula 102 that is a hollow member having a guide bore 115 (See FIG. 14), an obturator 103 having a distal part 103A formed as a sharp puncturing part, which is passed through the guide bore 115 of the cannula 102 so that the puncturing part can be removed and which punctures the abdominal wall 120, and a handpiece 104 to be attached freely detachably to the cannula 102.

Incorporated in the handpiece 104 are, as shown in FIG. 13, an ultrasonic transducer 106 serving as an ultrasound generating means, for example, a bolted Langevin transducer and a horn 117 coupled to the ultrasonic transducer 106. A threaded section 109 of the distal part of the obturator 103 can be freely detachably attached to the horn 117. If the obturator 103 is broken or the shape of the distal part 103A of the obturator 103 should be modified, the obturator 103 and handpiece 104 need not be replaced with another in one united body but the obturator 103 alone can be replaced with another independently of the handpiece 104. The ultrasonic transducer 106 has bipolar voltage input terminals. The vibration form may be either electrostriction or magnetostriction.

The ultrasonic transducer 106 converts electrical power of an ultrasonic frequency supplied from an ultrasonic oscillation apparatus 107 to ultrasonic vibrations. The ultrasonic vibrations are amplified by the horn 117 and propagated to the obturator 103. The distal part 103A of the obturator 103 vibrates at the ultrasonic frequency in an axial direction. The output of the ultrasonic oscillation apparatus 107 is controlled by an output control equipment 108 (for example, a foot switch or hand switch) shown in FIG. 12. For controlling the output of the ultrasonic oscillation apparatus 107, an output control switch may be located on the handpiece 104 or cannula 102.

As shown in FIG. 14, the distal part 103A of the obturator 103 is formed like an upside-down cone. A taper surface 111 having the same inclination as a taper surface 110 that is the lateral side of the conical distal part 103A of the obturator 103 is formed on the distal margin of the cannula 102. Once a quantity of jutting out the obturator 103 from the cannula 102 is determined so that the state shown in FIG. 14 can be attained, the obturator 103 and cannula 102 will not be stepped on the distal margin of the cannula 102 from which the obturator 103 juts out. Consequently, the obturator 103 and cannula 102 can be thrust into the abdominal wall 120 without any resistance.

As mentioned above, in the trocar 101 of the fourth embodiment, the obturator 103 and cannula 102 can be positioned in such a way that the obturator 103 and cannula 102 do not lie stepwise with the distal margin of the cannula 102 from which the obturator 103 juts out as a border.

Resistance against puncture is therefore small. Consequently, the trocar 101 can smoothly be inserted into the abdominal wall 120 with a readily controllable amount of force. It will therefore not take place that the trocar 101 is introduced into the deep end of the abdominal cavity.

Since the obturator 103 and cannula 102 are not stepped and the resistance against puncture is small, puncturing work can be accomplished for a short period of time. The time during which the vibrating obturator 103 is in contact with a living tissue can therefore be short. It will therefore not take place that the living tissue is thermally burnt with heat stemming from ultrasonic vibrations or frictional heat occurring between the living tissue and obturator 103 due to the ultrasonic vibrations.

Since the obturator 103 and cannula 102 are not stepped, the cannula 102 is thrust smoothly into the abdominal wall. The punctured region of the abdominal wall will not be injured severely but will be cured quite shortly after surgery.

Figure 15:
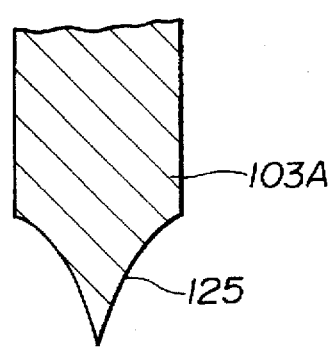
FIG. 15 is a sectional view showing the structure of the distal part of an obturator in an ultrasonic trocar of an ultrasonic trocar system in accordance with the fifth embodiment of the present invention.
Figure 16:
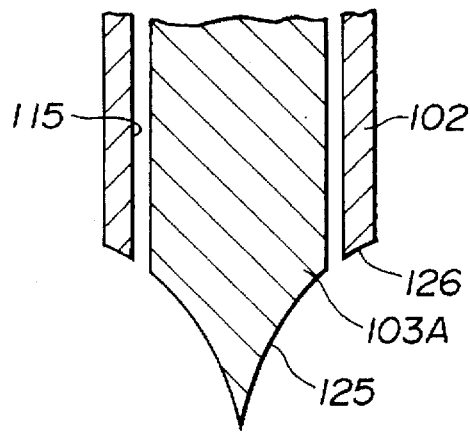
FIG. 16 is a sectional view showing an example of the structure of the distal part of a trocar with an obturator shown in FIG. 15 mounted in a cannula.

FIGS. 15 and 16 show the fifth embodiment of the present invention. Referring to FIG. 15, the distal part 103A of the obturator 103 of this embodiment has the lateral side of the upside-down cone dented smoothly inward. A curve (outline) 125 of the section of the distal part 103A continuously and smoothly extends like a curve representing an exponential function from the distal end of the distal part 103A to the proximal end thereof. The distal part 103A of the obturator 103 comes gradually into contact with a living tissue without any resistance so that a curved surface can spread with the needle-like tip of the distal part 103A as an origin. Resistance against puncture is smaller than that applied to the upside-down cone shown in FIG. 14.

Owing to the shape of the distal part 103A, a large amount of puncturing force is unnecessary for puncturing the abdominal wall 120 for the first time. The puncturing efficiency at the beginning of puncture is good. Besides, the puncturing efficiency thereafter is drastically improved because an area of the distal part in contact with a living tissue is smaller than that of the distal part shaped like an upside-down cone (See FIG. 14).

When the distal part 103A is shaped as shown in FIG. 15, even if the obturator 103 and cannula 102 are stepped, puncturing efficiency is improved more greatly than it is improved by a prior art. As shown in FIG. 16, once a curved surface 126 smoothly continuous to a curved surface, which shown as the curve 125 in FIG. 16, of the obturator 103 is formed on the distal margin of the cannula 102, if the obturator 103 and cannula 102 are positioned in such a way that the obturator 103 and cannula 102 do not lie stepwise with the distal margin of the cannula 102 as a border, the puncturing efficiency is improved incomparably with it is by the prior art, or improved more greatly than it is by the fourth embodiment. Needless to say, the time required for cure is shortened and a thermal burn can be avoided reliably.

Figure 17:
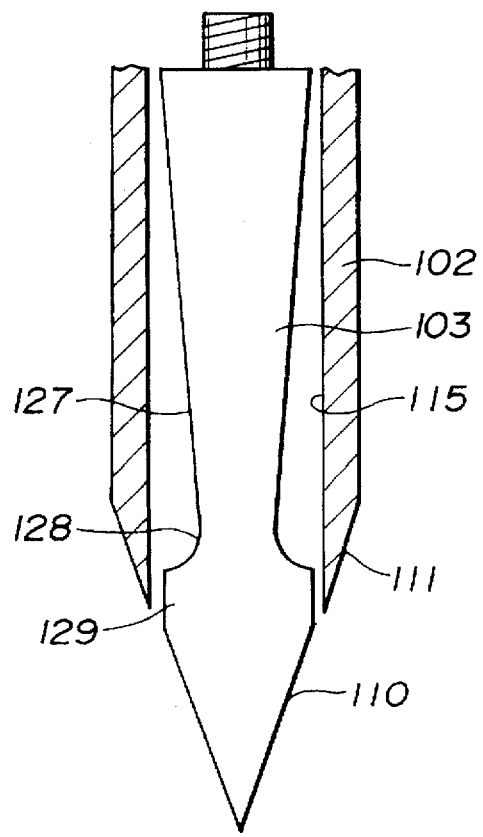
FIG. 17 is a sectional view showing the distal part of an ultrasonic trocar of an ultrasonic trocar system in accordance with the sixth embodiment of the present invention.

FIG. 17 shows the sixth embodiment of the present invention. An ultrasonic trocar in this embodiment has an obturator 103 thereof tapered toward the distal part. A taper surface 127 and distal part 103A are linked smoothly by a curved section 128. The shape of the distal part 103A is identical to that in the fourth embodiment. A portion between the curved section 128 and the taper surface 110 of the distal part 103A is formed as a columnar section 129 whose section is coaxial and parallel to a guide bore 115. The outer diameter of the columnar section 129 is equal to the maximum outer diameter of the obturator 103.

Once the obturator 103 is thus tapered, the amplitude of ultrasonic vibrations propagated from the ultrasonic transducer 106 can be enlarged. Moreover, once the obturator 103 is fitted in a cannula 102 so that the columnar section 129 can be positioned at the distal end of the cannula 102, it can be prevented that when the trocar is thrust into the abdominal wall 120, the center axis of the cannula 102 and the center axis of the obturator 103 are mismatched mutually, and eventually inserting efficiency deteriorates.

incidentally, if the obturator 103 is made of titanium, duralumin, or PTFE, the puncturing efficiency of the obturator 103 improves drastically. Moreover, the distal part 103A may be coated with PTFE. If the cannula 102 is made of stainless steel, dolman, or PTFE, or coated with PTFE, the ability of the cannula 102 to puncture a tissue improves.

Figure 18:
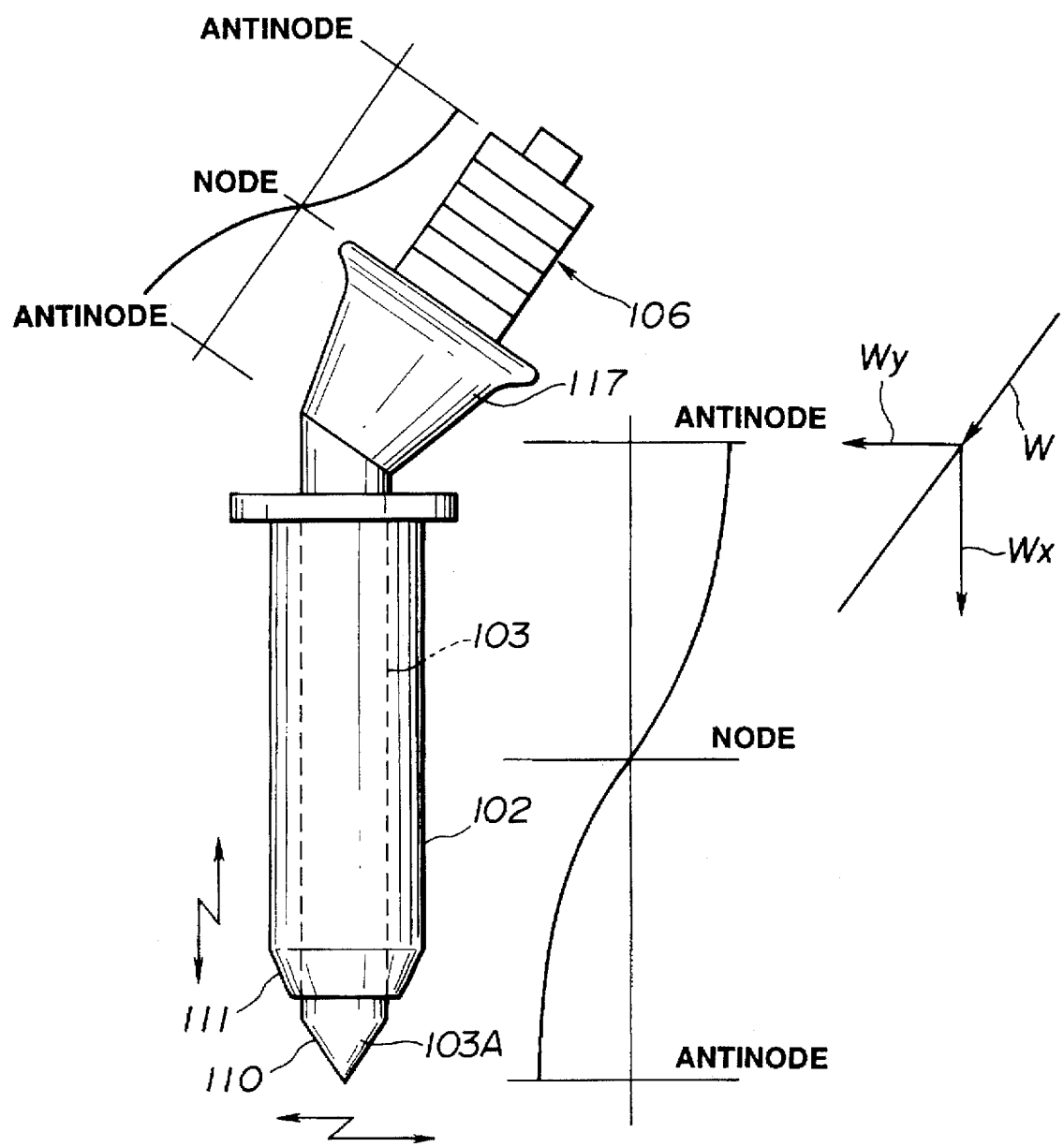
FIG. 18 is an explanatory diagram schematically showing an ultrasonic trocar system in accordance with the seventh embodiment of the present invention and the waveform of a driving wave.

FIG. 18 shows the seventh embodiment of the present invention. An ultrasonic trocar in this embodiment has a horn 117, which is coupled to an ultrasonic transducer 106, joined with the proximal end of an obturator 103 at an angle. The other components are identical to those in the fourth embodiment.

According to the foregoing structure, ultrasonic vibrations W generated by the ultrasonic transducer 106 are propagated at an angle with respect to the axial direction of the obturator 103 (direction of puncture). Consequently, an ultrasonic vibration W causes the obturator 103 to vibrate not only in a longitudinal direction (direction of puncture) but also in a transverse direction (direction perpendicular to the direction of puncture) so that a component Wx changing parallel to the direction of puncture of the obturator 103 as well as a component Wy changing perpendicularly to the direction of puncture can be produced. The waveform of an ultrasonic vibration W generated by the ultrasonic transducer 106 and the waveform of an ultrasonic vibration propagated to the obturator 103 are shown in FIG. 18.

Since the obturator 103 vibrates in the transverse direction, a tissue is split in the transverse direction by the obturator 103. This causes a puncture hole to expand. The closeness level between the obturator 103 and tissue deteriorates, whereby the ability of the trocar to puncture a tissue (inserting efficiency) improves. Moreover, since friction between the tissue and obturator 103 resulting from longitudinal vibrations diminishes, the tissue is prevented from being thermally burnt. Furthermore, only a reduced amount of puncturing force is needed.

Another method of vibrating the obturator 103 in the transverse direction includes a method utilizing a flexural transducer. Using the flexural transducer, the horn 117 coupled to the ultrasonic transducer 106 need not be joined with the obturator 103 at an angle.

An example of the circuitry of an obturator vibrating means utilizing the flexural transducer will be described in conjunction with FIGS. 19 to 22.

FIG. 20 shows the handpiece 104 including a flexural transducer. Semi-annular electrostriction devices 130 constituting the flexural transducer, each of which has an electrode terminal 131 inserted in the middle thereof, are tightly fixed to a metallic block 134 and horn 117 by a bolt 133. The horn 117 is, as described previously, joined with an obturator 103 that is not shown.

FIG. 21 illustrates the distribution of displacements in a flexural vibration, and FIG. 22 illustrates the distribution of displacements in a vibration made in an axial direction. Referring to FIG. 21, the electrostriction devices 130 are located up and down in the vicinity of the antinode of the distribution of displacements.

FIG. 19 shows the circuitry for producing the flexural vibrations. In the drawing, there are shown a common terminal 131A and driving power supply 132.

Aside from the flexural transducer, a torsion coupler type motor (a mode transducer type rotary motor using a torsion coupler) or a composite transducer type rotary motor can be used. This kind of motor allows the obturator 103 to make transverse vibrations.

Figure 23:
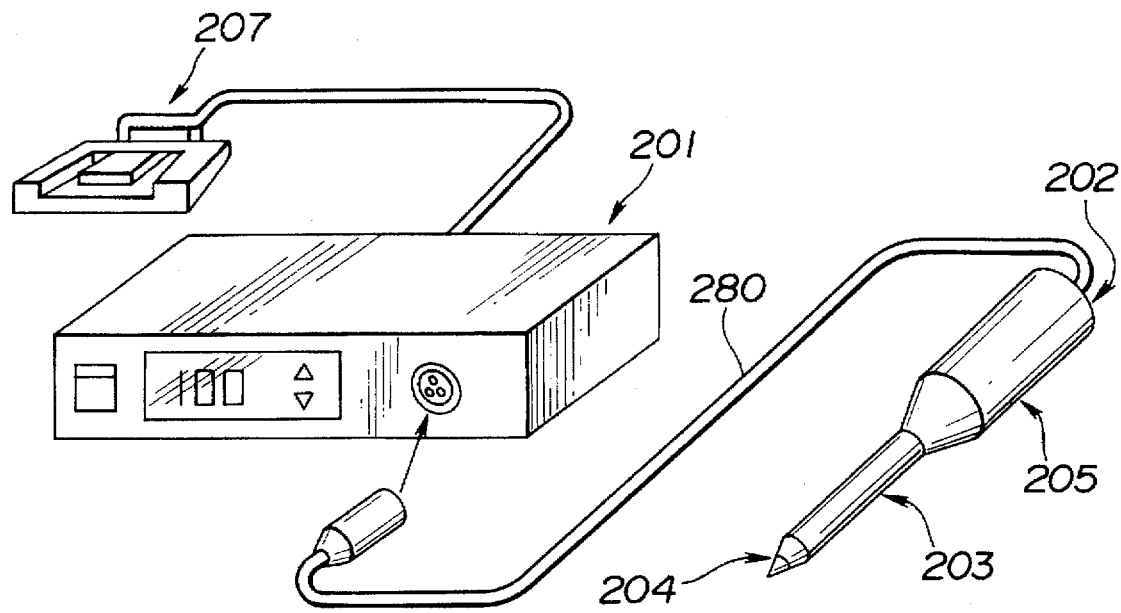
FIG. 23 is a schematic view showing the configuration of an ultrasonic trocar system in accordance with the eighth embodiment of the present invention.

FIGS. 23 to 26 show the eighth embodiment of the present invention. FIG. 23 is a diagram showing the configuration of a trocar system in which this embodiment is implemented.

The trocar system comprises a drive unit 201 serving as a driving means for generating electrical energy of an ultrasonic frequency, a trocar assembly 202 capable of being connected to the drive unit 201 over a cable 280, and a foot switch 207 serving as a switching means to be manipulated by an operator. The trocar assembly 202 includes a cannula 203, an obturator 204 serving as an elongated propagation member for propagating vibrational energy when brought into contact with a living tissue, and a handpiece 205 serving as a vibration generating means, connected to the obturator 204, for generating ultrasonic vibrational energy. Electrical energy generated by the drive unit 201 is supplied to the handpiece 205, whereby vibrational energy is generated.

Figure 24:
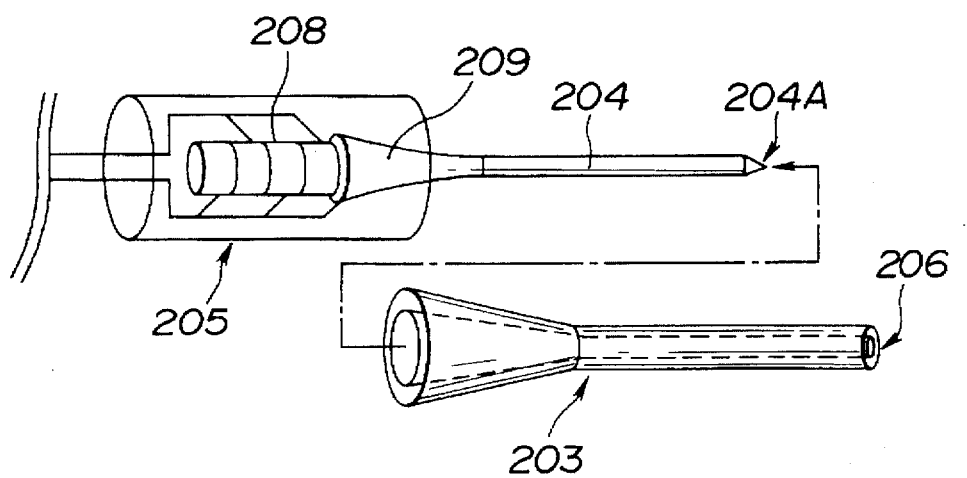
FIG. 24 is an explanatory diagram showing the detailed structure of a trocar assembly in the eighth embodiment.

FIG. 24 is a diagram showing the detailed structure of the trocar assembly 202 shown in FIG. 23. The handpiece 205 includes an ultrasonic transducer 209 composed of piezoelectric devices 208, and generates ultrasonic vibrational energy. The obturator 204 has a distal part 204A for puncturing the abdominal wall, has the back end thereof connected to the ultrasonic transducer 209 in the handpiece 205, and thus propagates ultrasonic vibrations to the distal part 204A. The cannula 203 has a guide bore 206 through which the obturator 204 is passed.

The operation of the configuration shown in FIGS. 23 and 24 will be described. First, the drive unit 201 generates electrical energy of an ultrasonic frequency, and transmits the electrical energy to the ultrasonic transducer 209 inside the handpiece 205 over the cable 280. The ultrasonic transducer 209 causes the piezoelectric devices 208 to convert the received electrical energy to mechanical vibrational energy, and vibrates the obturator 204. The vibrations propagate to the distal part 204A. The distal part 204A then applies a puncturing force to the abdominal wall in cooperation with the cannula 203, which contains the obturator 204 in the guide bore 206 thereof, whereby the distal part 204A punctures and splits the tissue, and then penetrates the abdominal wall. Vibrations to be produced by the ultrasonic transducer 209 can be turned ON or OFF by manipulating the foot switch 207.

Figure 25:
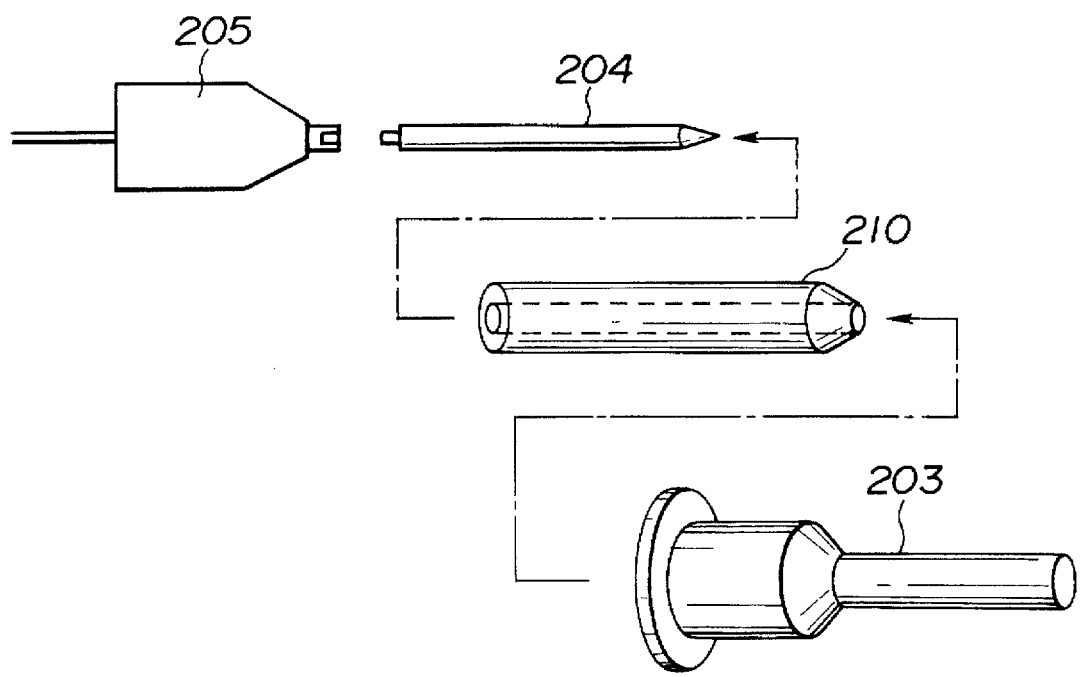
FIG. 25 is an explanatory diagram of the structure of the trocar assembly with an adaptor added, showing how to produce the trocar assembly in the eighth embodiment.

FIG. 25 shows the situation of assembling components including an adaptor 210 that is an intermediate member serving as a vibration control means so as to produce the trocar assembly 202. The obturator 204 is fixed tightly to the handpiece 205 using a screw or the like. The obturator 204 is encapsulated with the adaptor 210 made of a heat-resistive material, and then sheathed with the cannula 203.

Figure 26:
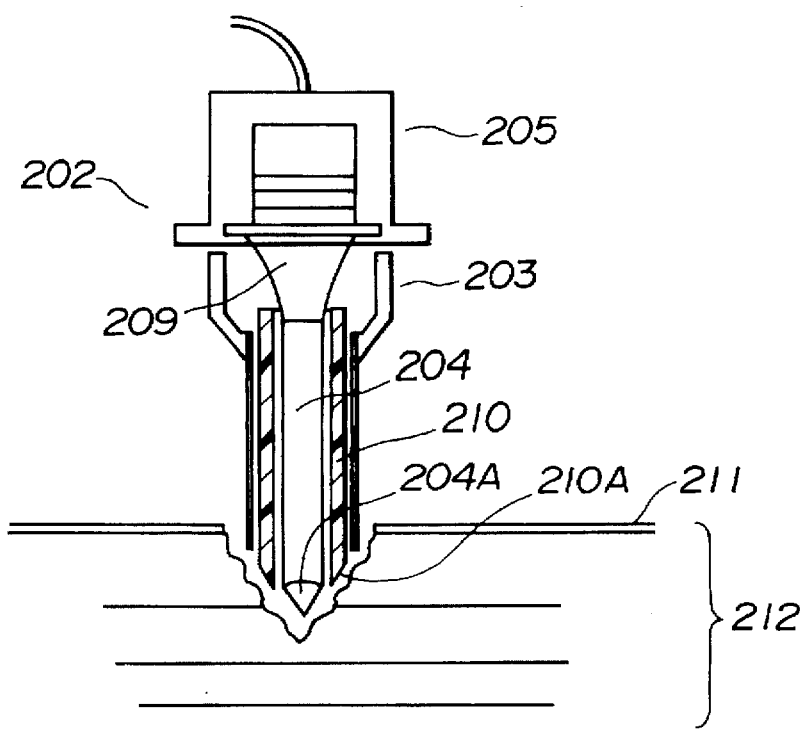
FIG. 26 is a sectional view showing a state in which the trocar assembly shown in FIG. 25 is about to penetrate the abdominal wall via the epidermis of a patient.

FIG. 26 is a sectional view showing a state in which the thus produced trocar assembly 202 is about to penetrate the abdominal wall 212 through the patient's epidermis 211. The adaptor 210 is interposed between the obturator 204 and cannula 203. A distal end 210A of the adaptor 210 has the diameter thereof varied continuously from a value corresponding to the outer diameter of the obturator 204 to a value corresponding to the inner diameter of the cannula 203.

The operation of the structure shown in FIGS. 25 and 26 will be described below.

First, a knife or the like is used to incise a small site of the epidermis 211 of the abdominal wall 212. Thereafter, the trocar assembly 202 is thrust into the abdominal wall 212. Ultrasonic vibrations generated by the ultrasonic transducer 209 propagate to the distal part 204A of the obturator 204. This cause the distal part 204A to split a tissue. When the trocar assembly 202 is further thrust forward, the incised site on the abdominal wall 212 is extended forcibly by the distal part 210A of the adaptor 210 whose diameter gets larger step by step. Finally, the distal part 204A of the obturator 204 penetrates the abdominal wall. The incised site on the abdominal wall is further extended as wide as the outer diameter of the cannula 203 by the distal part 210A of the adaptor 210. Finally, the cannula 203 penetrates the abdominal wall 212. Puncture is completed.

In the process ending with penetration, after the distal part 204A of the obturator 204 vibrating at an ultrasonic frequency comes into contact with the tissue of the abdominal wall 212 and forms a puncture hole, the distal part 210A of the adaptor 210 not vibrating at the ultrasonic frequency widens the hole on the abdominal wall 212. Therefore, a thermal burn will not occur at that site. The adaptor 210 is made of a nonmetallic material such as PTFE. When the distal part 204A of the obturator 204 has the tip thereof sharpened to some extent, the peritoneum that is the last obstruction to penetration of the abdominal wall 212 can be torn easily.

According to the eighth embodiment, in the process ending with penetration, the period during which the obturator is in contact with a living tissue is minimized. Vibrational energy whose level is equal to or larger than a permissible level is not propagated to the living tissue. Consequently, the living tissue can be protected from a thermal injury.

Figure 27:
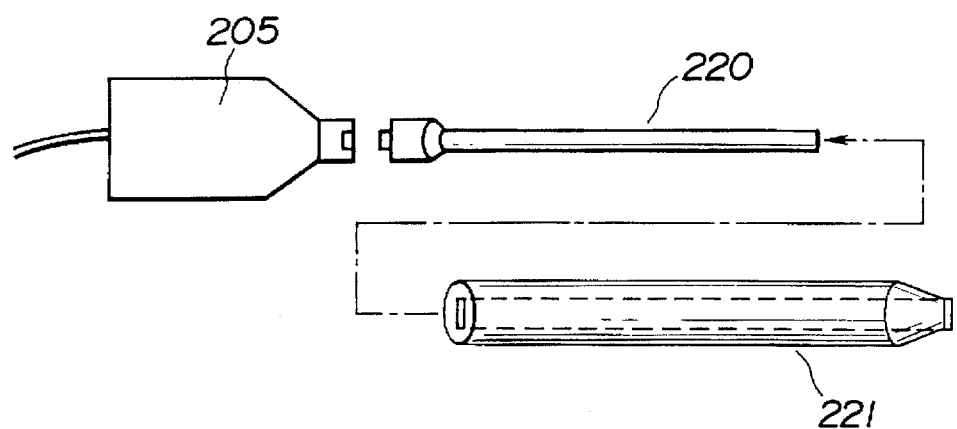
FIG. 27 is a schematic view showing the structure of the first variant of the trocar assembly.
Figure 28:
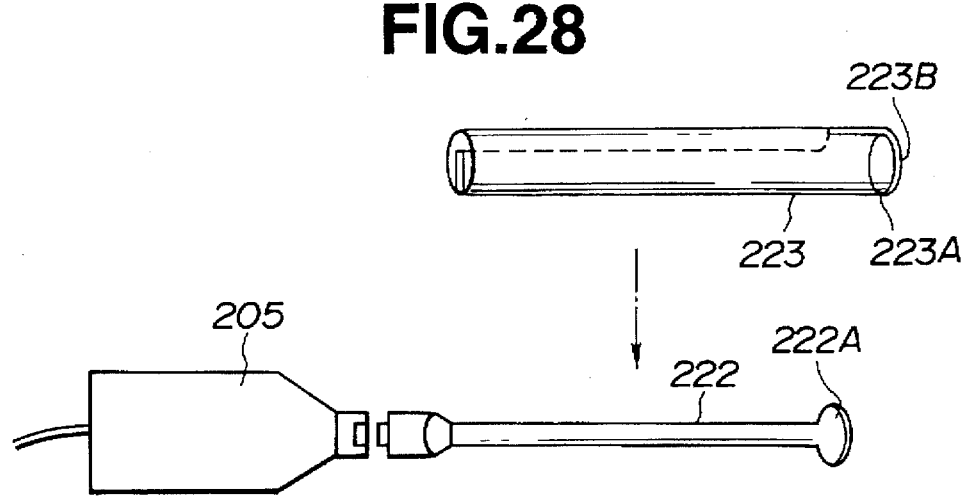
FIG. 28 is a schematic view showing the structure of the second variant of the trocar assembly.
Figure 29:
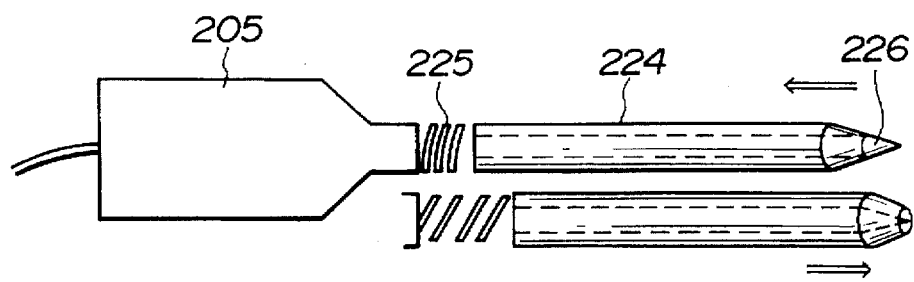
FIG. 29 is a schematic view showing the structure of the third variant of the trocar assembly.

FIGS. 27 to 29 show variants of the eighth embodiment.

Referring to FIG. 27, a trocar assembly 202 of the first variant is characterized by an elongated plate-like obturator 220, and an adaptor 221 having a lumen into which the obturator 220 can be inserted and capable of being passed through a cannula 203. In this variant, as shown in FIG. 27, the obturator 220 is inserted into the adaptor 221 with the distal end thereof as the head.

Referring to FIG. 28, a trocar assembly 202 of the second variant includes a plate-like obturator 222 having a distal part 222A thereof machined like a bow, and an adaptor 223 having a distal part 223A thereof shaped like a hemisphere, and including a slit 223B through which the distal part 222A of the obturator 222 can jut out a bit. In this variant, as shown in FIG. 28, the adaptor 223 is mounted from above the obturator 222.

The operations of the structures shown in FIGS. 27 and 28 are the same as those already described. Preferably, the distal parts of the plate-like obturators 220 and 222 should have the tips thereof sharpened to some extent so that they can penetrate the peritoneum existing as the last obstruction to penetration of the abdominal wall.

FIG. 29 shows the third variant. Referring to FIG. 29, a stretching and contracting spring member 225 is interposed between an adaptor 224 and handpiece 205. When a trocar assembly 202 is thrust into the abdominal wall 212, the adaptor 224 withdraws and the tip of an obturator 226 juts out to enable puncture. When the pressure applied to the adaptor 224 weakens, the force exerted by the spring member 225 causes the adaptor 224 to advance to cover the distal part of the obturator 226. Owing to this structure, after the distal part of the obturator 226 splits the tissue of the abdominal wall and punctures it, the adaptor 224 isolates the obturator 226 from the living tissue. The obturator 226 will therefore not be in contact with the living tissue for an unnecessarily long time. Consequently, a thermal burn can be avoided.

The ninth embodiment of the present invention will be described with reference to FIG. 30 below.

Figure 30:
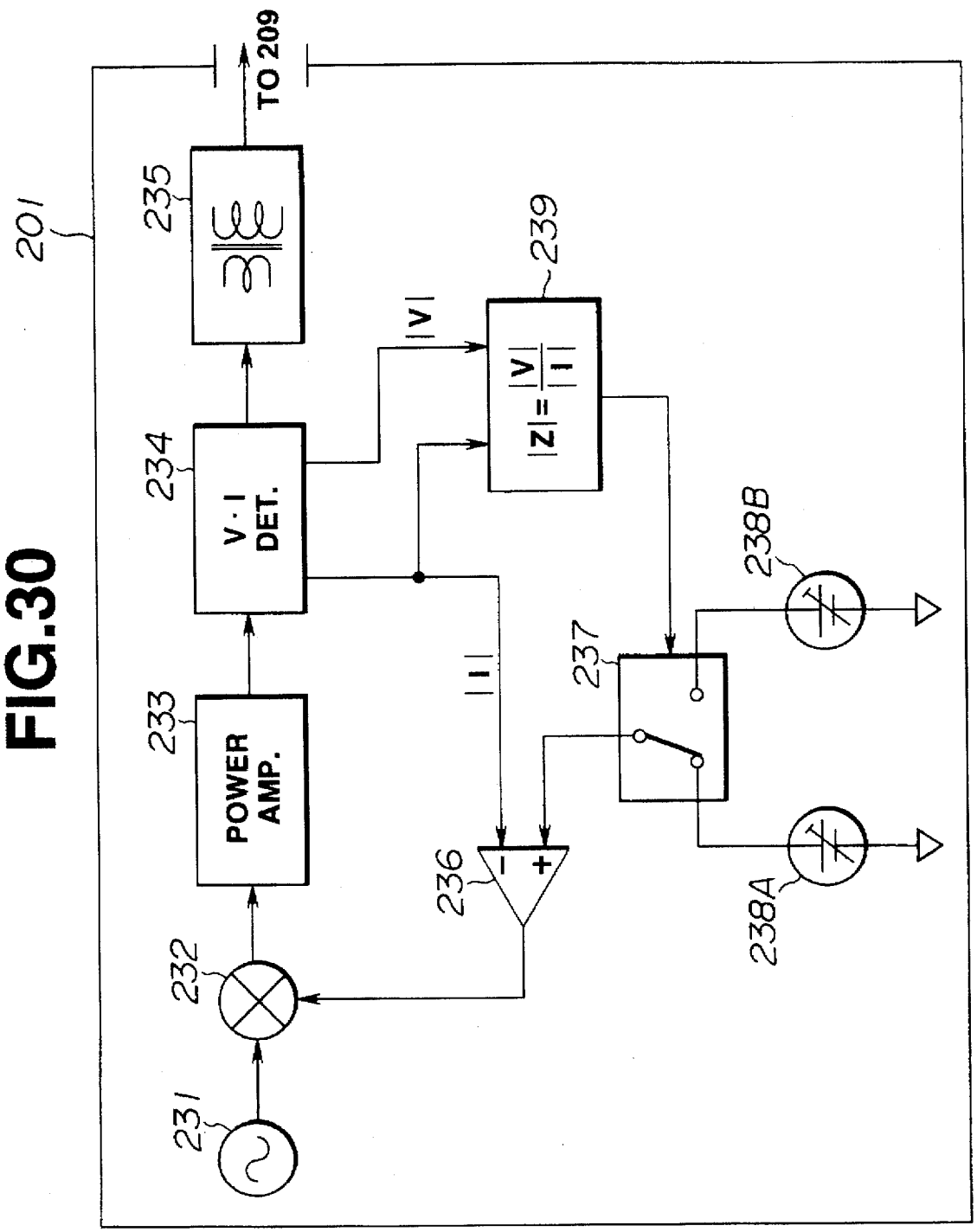
FIG. 30 is a block diagram showing the circuitry of a drive unit in accordance with the ninth embodiment of the present invention.

FIG. 30 is a diagram showing the circuitry of the drive unit 201 shown in FIG. 23. The drive unit 201 comprises an oscillatory circuit 231 for generating an electrical signal of an ultrasonic frequency, a multiplier 232, a power amplifier 233 for amplifying in power the electrical signal of the ultrasonic frequency, a current/voltage detection circuit 234 for detecting an amplified current and voltage, a transformer 235 designed for boosting and insulation, a comparator 236 for comparing the voltage of a signal indicating a detected magnitude of a current with a signal indicating a set current value, and sending the result of the comparison to the multiplier 232, a switching circuit 237 for switching signals indicating set current values to be fed to the comparator 236, reference circuits 238A and 238B each generating a signal indicating a set current value, and an arithmetic circuit 239 for computing the magnitude of a load, that is, an impedance using a signal indicating the magnitude of a voltage and a signal indicating the magnitude of a current which are sent from the current/voltage detection circuit 234.

The operation of the circuitry shown in FIG. 30 will be described below. The amplitude of vibrations produced by the ultrasonic transducer 209 (not shown in FIG. 30) is proportional to the magnitude of a flowing current. By controlling the current so that the magnitude of the current can remain constant, a steady constant amplitude of vibrations can be attained irrespective of the variation of a load applied to the ultrasonic transducer 209.

A signal indicating the magnitude of a current detected by the current/voltage detection circuit 234 is compared with a signal serving as a reference to be set by the reference circuit 238A or 238B by means of the comparator 236. The result of the comparison is fed back to the multiplier 232, whereby constant current control is carried out. That is to say, a current is maintained constant by varying the magnitude of a voltage applied to the ultrasonic transducer 209. The magnitudes of a voltage and current are detected by the current/voltage detection circuit 234. The arithmetic circuit 239 then divides the current value by the voltage value so as to calculate an impedance. The switching circuit 237 switches either the reference circuit 238A or 238B over to the comparator 236, whereby the reference circuit 238A is used to increase the set current value, that is, the amplitude set in the ultrasonic transducer 209 according to the magnitude of the impedance, or the reference circuit 238B is used to decrease the amplitude set in the ultrasonic transducer 209.

The magnitude of the impedance calculated through the computation implies the state of a load imposed on the ultrasonic transducer 209, that is, a load applied to the distal part 204A of the obturator 204. Owing to the foregoing circuitry, the set amplitude of vibrations is controlled automatically: when the load on the obturator is large, the set amplitude of vibrations is increased; and when the load on the obturator is small, the set amplitude of vibrations is decreased.

Figure 31:
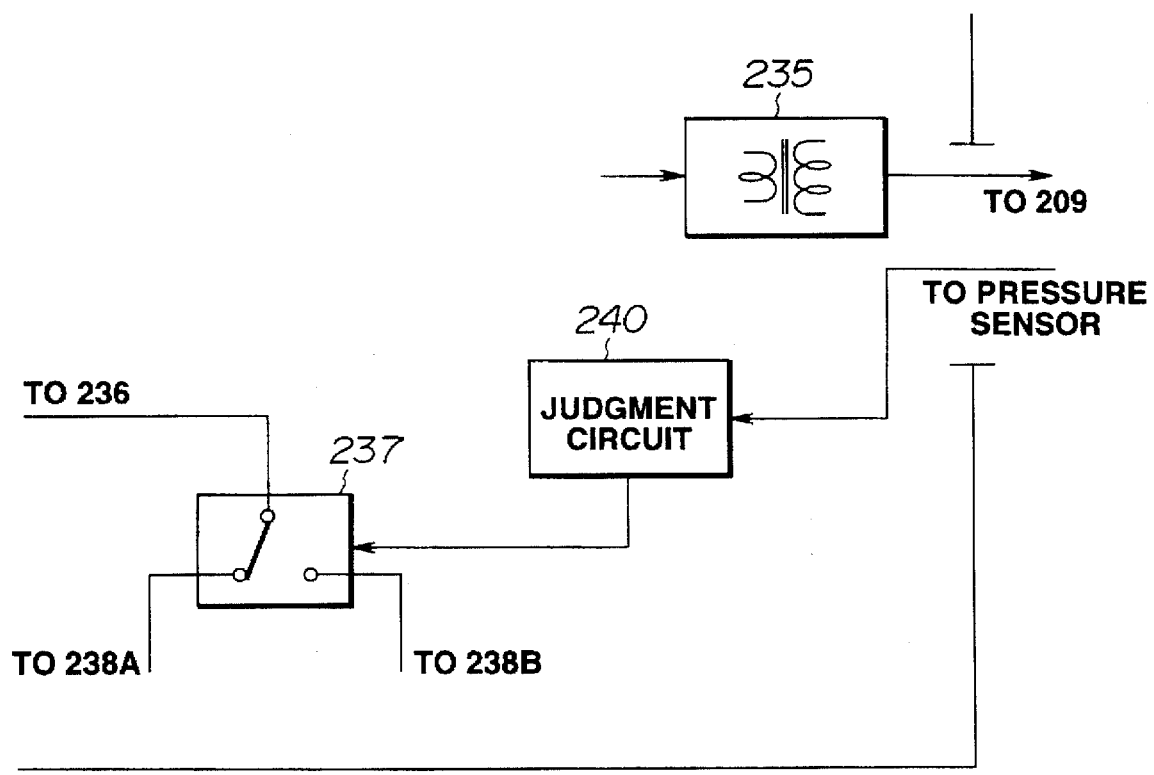
FIG. 31 is a block diagram showing the circuitry of a variant of the ninth embodiment.

FIG. 31 is a diagram showing a variant of the ninth embodiment.

In this variant, a pressure sensor for monitoring the state of a pressure load imposed on an obturator shall be incorporated in the ultrasonic transducer 209. Based on the output of the pressure sensor, the switching circuit 237 is switched by a judgment circuit 240.

To be more specific, when the pressure applied to the tip of an obturator is large, the reference circuit 238A is selected in order to increase the set value of the amplitude of vibrations. When the pressure is small, the reference circuit 238B is selected in order to decrease the set value of the amplitude of vibrations. Owing to this circuitry, when the pressure for puncture is high, a large amplitude is maintained. Thus, a tissue can be split quickly in order to create a puncture hole smoothly. Eventually, a trocar assembly can be inserted with a reduced amount of puncturing force.

By contrast, when the pressure for puncture must be lowered, the amplitude is held low. Thus, a tissue can be protected from a thermal burn. In other words, in the process of thrusting the trocar assembly into the abdominal wall, the obturator vibrating at a large amplitude is controlled so that it can not abut on the tissue of the abdominal wall unnecessarily closely. A thermal burn on the tissue of the abdominal wall can therefore be minimized.

Figure 32:
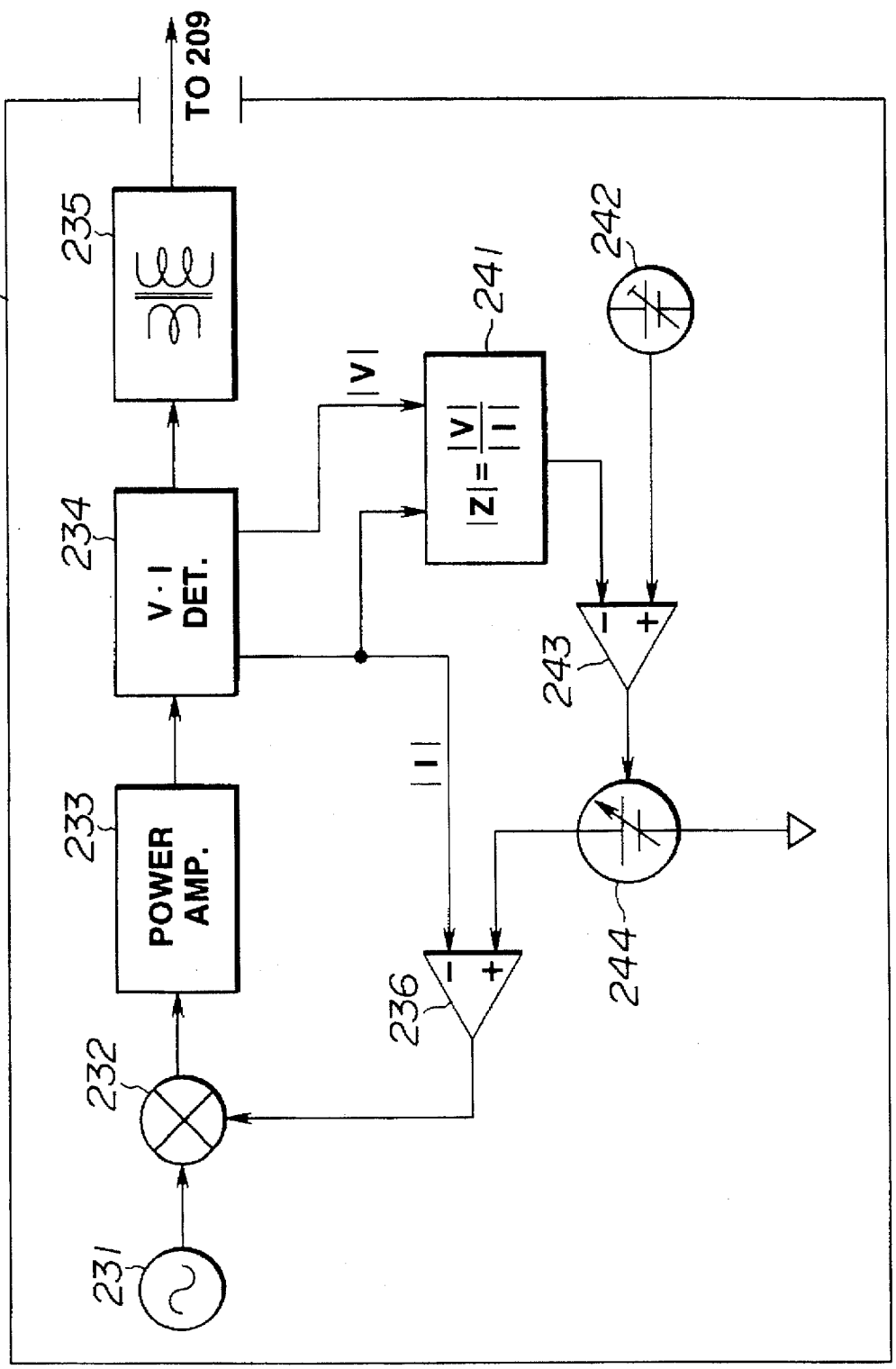
FIG. 32 is a block diagram showing the circuitry of a drive unit in accordance with the tenth embodiment of the present invention.

Referring to FIG. 32, the tenth embodiment of the present invention will be described below.

In FIG. 32, components identical to those of the ninth embodiment shown in FIG. 30 are assigned the same reference numerals. The description of the components will be omitted. A difference from the ninth embodiment shown in FIG. 30 lies in that the tenth embodiment includes an arithmetic circuit 241 for producing a signal indicating the magnitude of an impedance using signals indicating the magnitudes of a voltage and current detected by the current/voltage detection circuit 234, a reference circuit 242 for producing a signal indicating the magnitude of an impedance which is a control target value, a comparator 243 for comparing a signal provided by the arithmetic circuit 241 with a signal provided by the reference circuit 242 and outputting the result of the comparison, and a production circuit 244 for continuously producing a signal for use in setting the value of a current flowing to the ultrasonic transducer 209 on the basis of the output signal of the comparator.

The operation of the circuitry shown in FIG. 32 will be described. A current flowing into the ultrasonic transducer 209 is controlled to have a value indicated by the production circuit 244 by means of a feedback circuit including the comparator 236, multiplier 232, and current/voltage detection circuit 234. In short, constant current control is carried out.

Herein, the production circuit 244 can vary the current value continuously. The variation is determined through constant impedance control. That is to say, the arithmetic circuit 241 computes signals sent from the current/voltage detection circuit 234 so as to calculate the magnitude of an impedance. The impedance value implies the state of a load imposed on the tip of the obturator. The impedance value is compared with a target output value of the reference circuit 242, and fed back to the production circuit 244 until the impedance value becomes substantially constant.

Owing to the circuitry, when a load on the obturator seems to be too heavy, control is given so that the set value of an amplitude can get larger. This results in the improved ability to split a living tissue. Consequently, the load on the obturator is lightened. By contrast, when the load seems to be too light, control is given so that the set value of the amplitude can decrease. The amplitude of the obturator is thus lowered to a necessary sufficient value.

Figure 33:
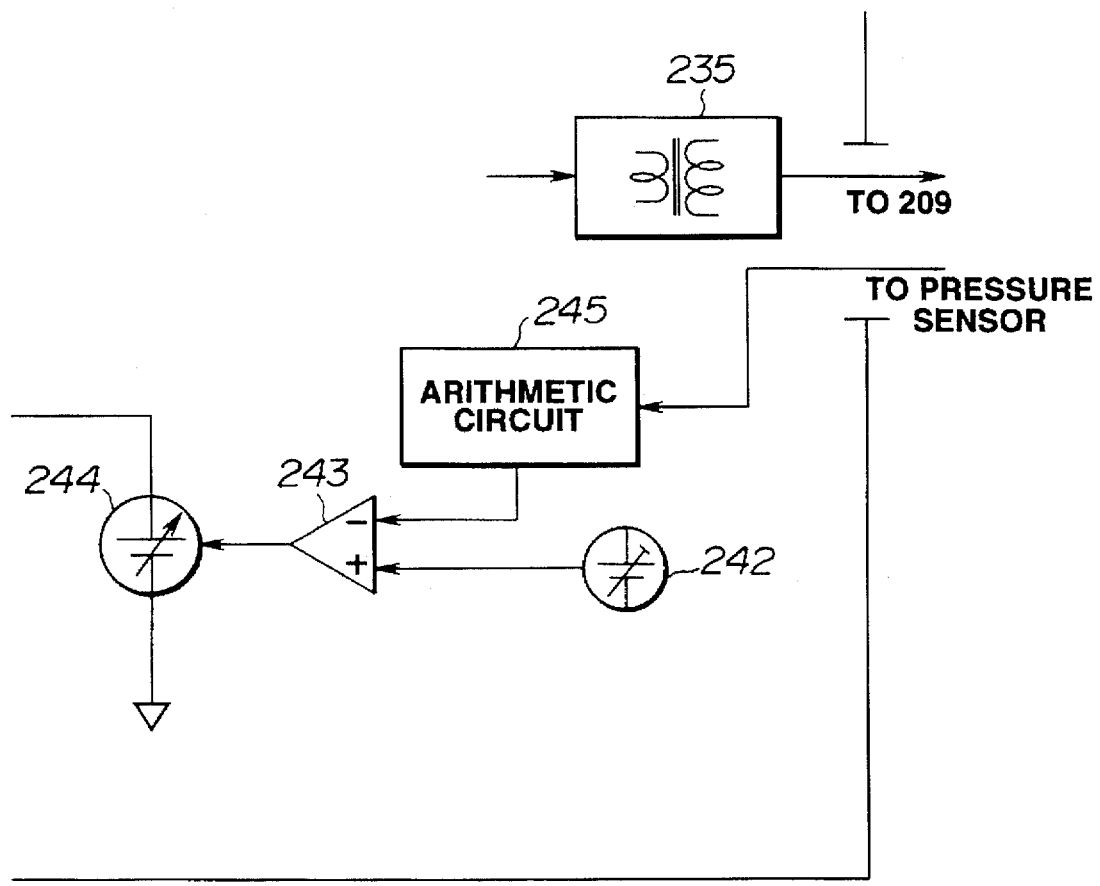
FIG. 33 is a block diagram showing the circuitry of a variant of the tenth embodiment.

FIG. 33 is a diagram showing a variant of the tenth embodiment. In this variant, a pressure sensor for detecting the state of a pressure load imposed on an obturator shall be incorporated in the ultrasonic transducer 209. The output of the pressure sensor is converted into a signal indicating the magnitude of a pressure by an arithmetic circuit 245 shown in FIG. 33. The result of the conversion is used as a feedback signal by a comparator 243, whereby a value indicated by a production circuit 244 is varied. Owing to this circuitry, constant voltage control is carried out: the set value of an amplitude is changed continuously until the pressure at the tip of the obturator becomes substantially constant.

According to the foregoing circuitry, the amplitude of vibrations is set to an optimal value according to a puncturing force exerted for puncture. Consequently, an ultrasonic trocar capable of being thrust into a living body while preventing occurrence of a thermal burn on a living tissue can be provided. Specifically, the amplitude of vibrations made by the distal part of a trocar assembly varies in real time depending on the magnitude of a pressure applied to the distal part. When the pressure for puncture is too low, since the amplitude is small, occurrence of frictional heat whose level is unnecessarily high can be prevented. When an operator is applying a puncturing force in an attempt to thrust the trocar assembly into the tissue, the distal part vibrates at a high amplitude. This enables smooth puncture.

Figure 34:
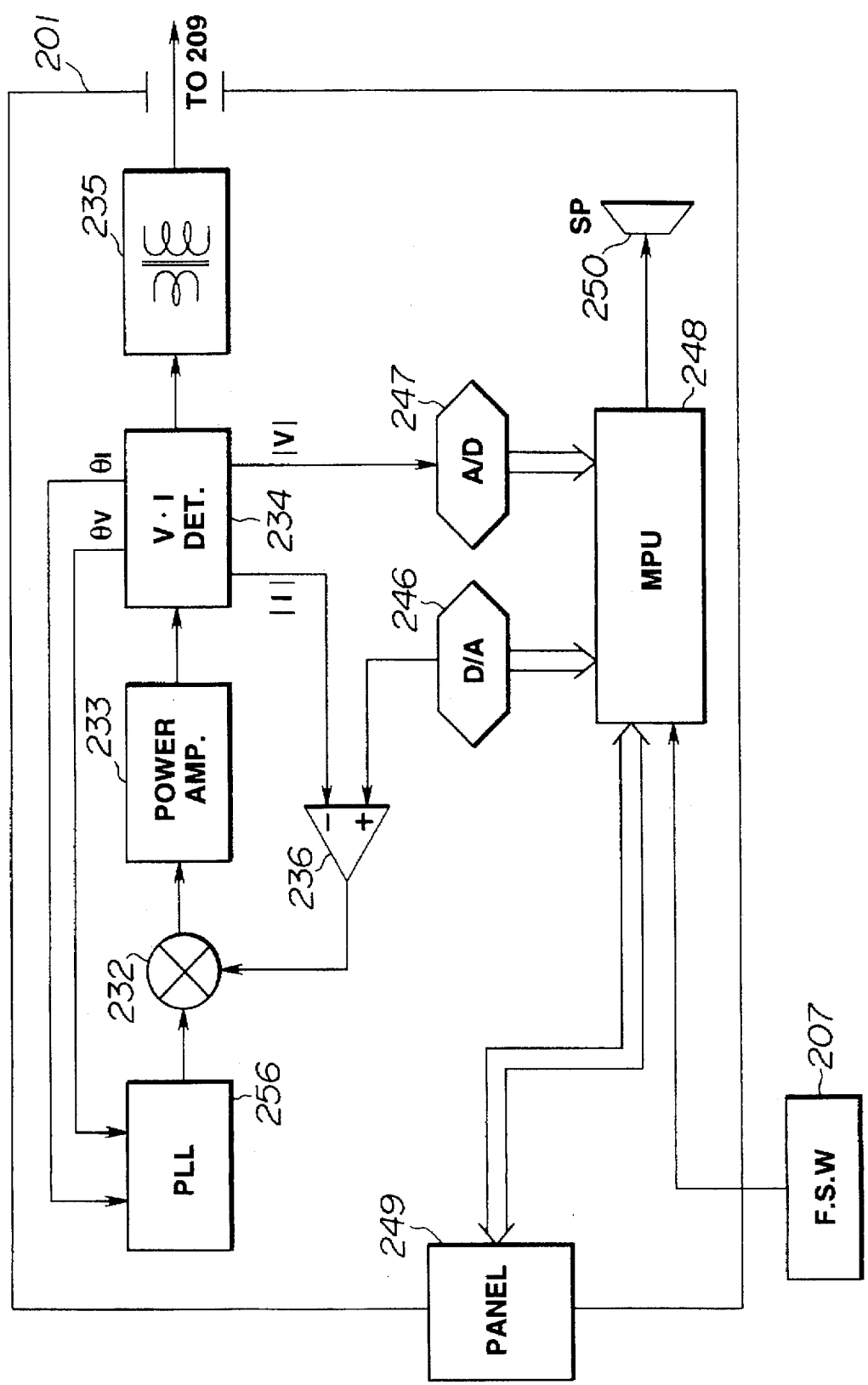
FIG. 34 is a block diagram showing the circuitry of a drive unit in accordance with the eleventh embodiment of the present invention.

Referring to FIG. 34, the eleventh embodiment of the present invention will be described below. Components identical to those shown in FIG. 30 are assigned the same reference numerals. The description of the components will be omitted. A difference from the circuitry shown in FIG. 30 lies in a point that the circuitry of this embodiment includes a phase-locked loop (PLL) 256 for controlling an output frequency on the basis of phase information concerning a current and voltage detected by a current/voltage detection circuit 234 so that a phase shift between the current and voltage can be 0°, a D/A converter 246 for outputting a set current value to a constant current control circuit, an A/D converter 247 for fetching a signal indicating the magnitude of a voltage, a microprocessor unit (MPU) 248 for controlling all the components, a display panel 249 at which an operator enters a set value and which displays the state of a system, and a speaker 250 for giving sound.

The operation of the circuitry shown in FIG. 34 will be described. When a foot switch (F.S.W) 207 is manipulated, an operation starts. The microprocessor unit 248 sends data to the D/A converter 246 so that the transducer can be driven with a current of a certain set value. With the current of the value, vibrations of a steady amplitude are started by the constant current control circuit. At this time, the PLL 256 works so as to carry out a resonant point tracking operation in which a frequency at which a phase shift between a current and voltage becomes 0 is determined so that a frequency informed owing to the work of the PLL 256 will agree with a resonance frequency at which the transducer produces vibrations most effectively.

When a load is imposed on the obturator, an impedance rises. At this time, the constant current control circuit works to keep a current value constant. An applied voltage therefore rises. The voltage rise is monitored by the A/D converter 247.

The microprocessor unit 248 then becomes aware of the fact that the impedance has risen, and updates data to be sent to the D/A converter so as to raise a set current value. If the load gets smaller and the voltage value drops, the A/D converter 247 detects the fact. The microprocessor unit 248 lowers the value of data to be sent to the D/A converter 246 so as to reduce the amplitude.

Thus, the set value of an amplitude is automatically changed according to the situation of a load imposed on an obturator. At this time, sound modulated according to the magnitude of a load judged by the microprocessor unit 248 may be output from the speaker 250. Alternatively, the display panel 249 presents display that varies depending on the magnitude of a load. Thus, an operator is informed of the state of a load.

Ultrasonic vibrations are stopped immediately when manipulation of the foot switch 207 is ceased.

According to the foregoing eleventh embodiment, an amplitude of ultrasonic vibrations suitable for the situation of a load can be obtained. Moreover, since an operator is informed of the situation of the load, safer puncture can be achieved under the operator's control. Incidentally, computation performed within the microprocessor unit 248 may be fast computation to be performed to make an impedance substantially constant. Alternatively, a memory map may be created in advance, and data supplied from the A/D converter 247 and D/A converter 247 may be used to specify control values. This way of control will also do.

Figure 35:
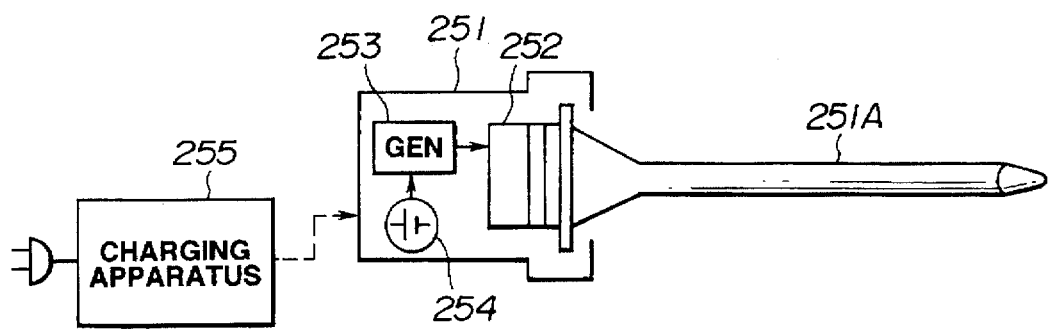
FIG. 35 is a schematic view showing the configuration of an obturator system in accordance with the twelfth embodiment of the present invention.

FIG. 35 is a diagram showing the configuration of the twelfth embodiment of the present invention.

The twelfth embodiment is an example of the configuration of an obturator system 251 with an operation aid. There is shown a vibrating obturator 251A. The obturator 251A is used while inserted into a cannula (not shown in FIG. 35) of an existing trocar. The obturator system 251 includes an ultrasonic transducer 252, drive circuit 253, and chargeable power supply 254. A charging apparatus 255 for charging is connected to the obturator system 251. Owing to the charging apparatus 255, energy is accumulated in the chargeable power supply 254.

When the obturator 251A is inserted into a cannula and pressed on the abdominal wall, a load rises. The drive circuit 253 therefore works so as to raise an amplitude set in the ultrasonic transducer 252. The obturator 251A is then thrust into the abdominal wall. After penetrating the abdominal wall, the obturator 251A is pulled back while the cannula is left in place and utilized. The obturator 251A is inserted into another cannula, and then maneuvered for puncture.

When the puncturing maneuver is not carried out, the load on the obturator 251A is small. Accordingly, the drive circuit 253 sets a small value as an amplitude in the transducer. Thus, safety is ensured. When the chargeable power supply 254 runs out of energy, it is charged. This permits repeated use. A battery of another type may be employed on behalf of the chargeable power supply 254.

Depending on a load applied to the tip of the obturator 251A, the always operating drive circuit 253 varies the amplitude at which the obturator 251A is vibrated.

According to this configuration, a switching mechanism for turning ON or OFF the drive of the obturator 251A becomes unnecessary. An obturator system can be configured using an obturator as a unit. When no load is applied to the tip of the obturator 251A, vibrations made by the obturator system 251 are not large. Even if the obturator 251A comes into contact with a living tissue, there is no concern about a burn or the like.

Referring to FIGS. 36A, 36B, 37A, and 37B, variants of the distal part of an obturator will be described below.

Figure 36A:
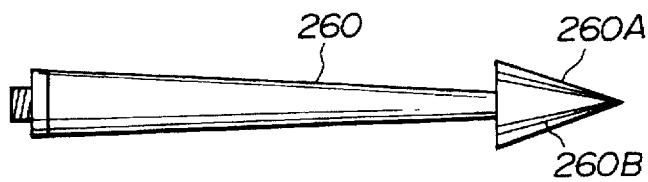
FIGS. 36A and 36B show the first variant of the distal part of an obturator.
Figure 36B:
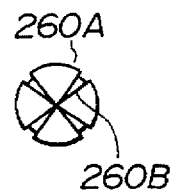
Figure 37A:
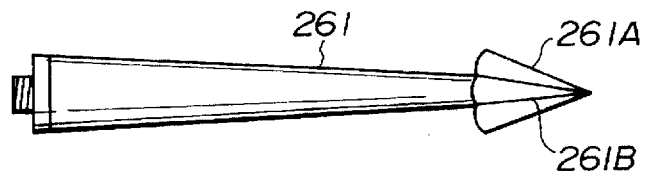
FIGS. 37A and 37B show the second variant of the distal part of an obturator.
Figure 37B:
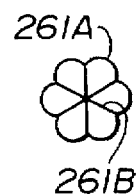

The first variant shown in FIGS. 36A and 36B is characterized in that a distal part 260A of an obturator 260 is shaped like a cone, and grooves 260B are formed on the conical surface. FIG. 36B is a view of the distal part 260A seen from the tip thereof. In the second variant shown in FIGS. 37A and 37B, an obturator 261 has a distal part 261A shaped like another kind of cone. Grooves 261B are formed on the distal part 261A. FIG. 37B is a view of the distal part 261A seen from the tip thereof. The distal part 261A is shaped like chrysanthemum.

The distal parts 260A and 261A are thus shaped like a cone, and the grooves 260B and 261B are formed on the conical surfaces. The area of a portion of each distal part in contact with a living tissue is therefore limited. A living tissue is extended as wide as the maximum outer diameter of the cone, whereby a puncture hole is formed. However, the portion of the conical surface in contact with the living tissue during formation of the puncture hole is so small that the possibility of a thermal burn due to friction can be suppressed.

Figure 38:
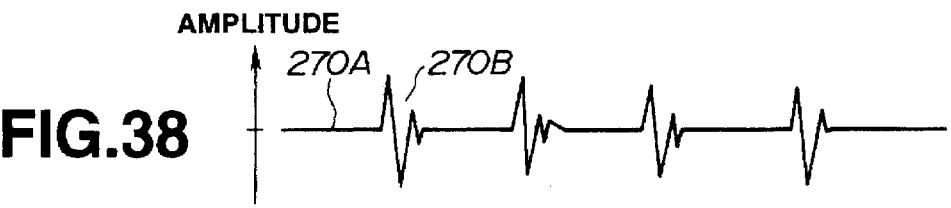
FIG. 38 is a waveform chart showing the first variant of a driving method for an obturator.
Figure 39:
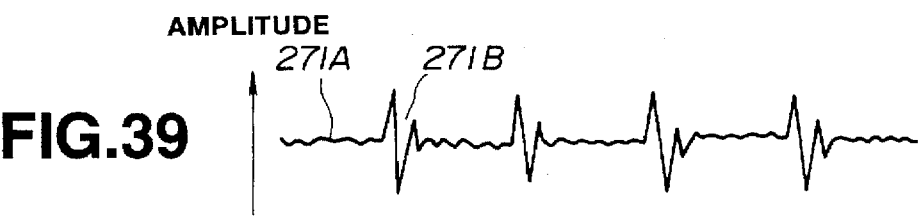
FIG. 39 is a waveform chart showing the second variant of the driving method for an obturator.

Referring to FIGS. 38 and 39, variants of the driving method for an obturator in this embodiment will be described. FIGS. 38 and 39 are diagrams each showing the amplitudes of ultrasonic vibrations. In the first variant shown in FIG. 38, the obturator is vibrated in such a way that: it does not vibrate for a certain period (270A), then vibrates for a short period (270B), and does not vibrate again for a certain period. In the second variant shown in FIG. 39, the obturator is vibrated continuously at a low amplitude for idling (271A), then vibrated at a high amplitude in a pulsed manner (271B), and again vibrated at the low amplitude for idling.

Owing to the driving method causing the obturator to repeat the above operation, the obturator that vibrates at an ultrasonic frequency vibrates intermittently during a period during which the obturator is in contact with a living tissue. Heating resulting from friction between the tip of the obturator and a living tissue therefore takes place only during a short period of time. Moreover, since there is a pause between a vibration and a subsequent vibration, heating is subsided during the pause period. It is therefore possible to prevent occurrence of a thermal burn on a living tissue. The driving method can be realized by providing the obturator intermittently with an amplitude setting signal produced by the constant amplitude control circuit in any of the aforesaid embodiments.

Figure 40:
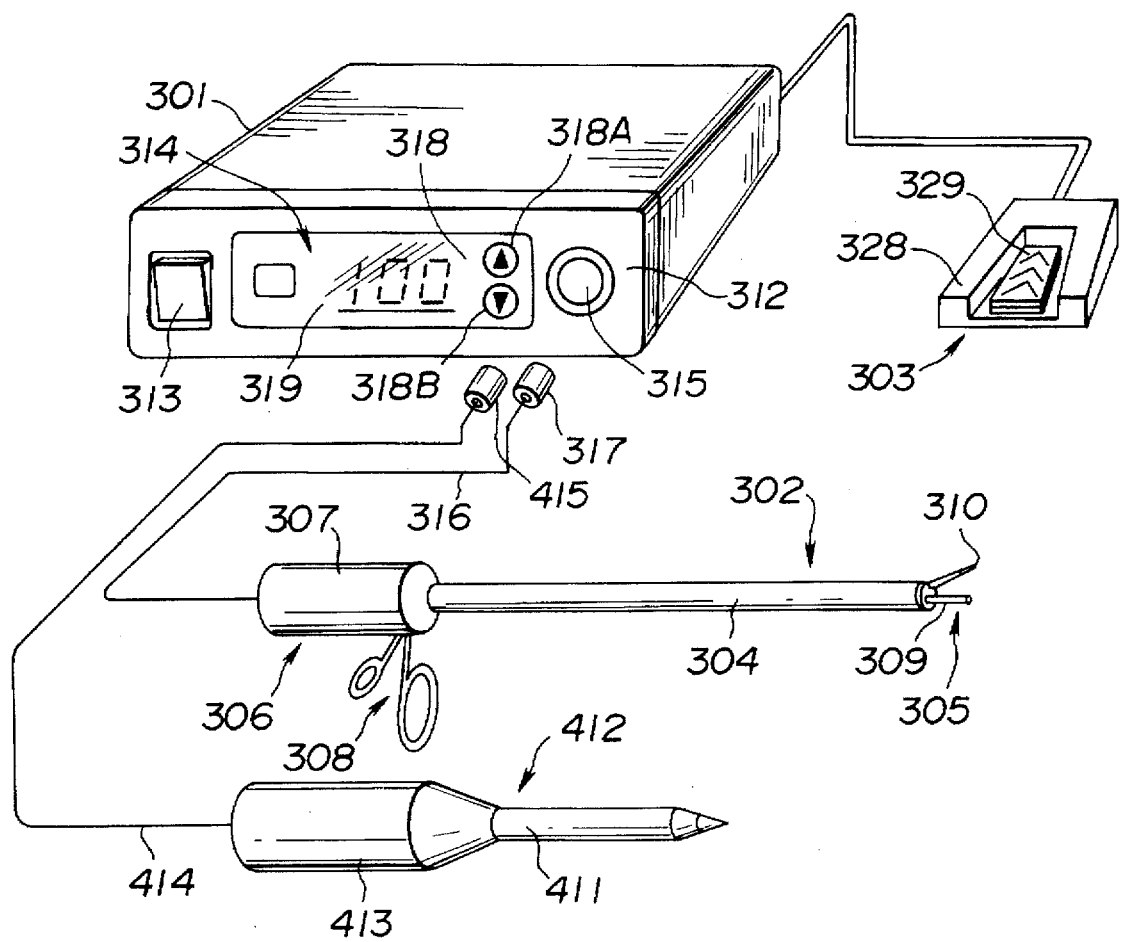
FIG. 40 is an oblique view schematically showing the overall configuration of an ultrasonic surgery system in accordance with the thirteenth embodiment of the present invention.

The thirteenth embodiment of the present invention will be described with reference to FIGS. 40 to 46. FIG. 40 shows the appearance of a whole ultrasonic surgery system of this embodiment.

A handpiece 302 and foot switch (switch means) 303 are connected to a main unit (drive unit) 301 of the ultrasonic surgery system of this embodiment.

The handpiece 302 has a therapeutic part 305 distally of an elongated sheath 304 and has an operating part 306 proximally thereof on the side of an operator's hand. The operating part 306 includes a case 307 for accommodating an ultrasonic transducer, which is not shown, for generating ultrasonic vibrations, and an operation handle 308.

Moreover, a probe 309 for propagating ultrasonic vibrations generated by the ultrasonic transducer to the therapeutic part 305 is included in the sheath 304. The distal part of the probe 309 is exposed to outside through the distal end of the sheath 304.

Figure 41:
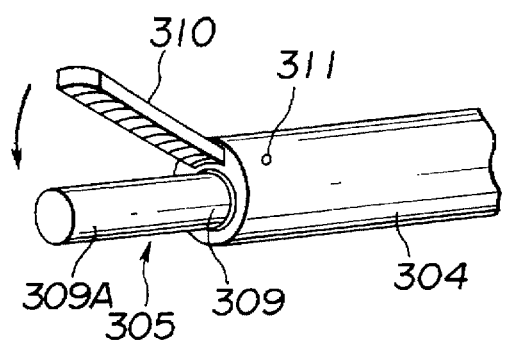
FIG. 41 is an oblique view showing the structure of a therapeutic part as a distal part of a handpiece in the ultrasonic surgery system of the thirteenth embodiment.

The therapeutic part 305 includes, as shown in FIG. 41, a clamp 310 to be driven to part from and meet with a distal exposed part 309A of the probe 309. The clamp 310 is coupled to the distal end of the sheath 304 so that it can pivot with a rotation pin 311 as a center. By manipulating the operation handle 308, the clamp 310 is driven to part from or meet with the distal exposed part 309A of the probe 309. Thus, a living tissue can be caught by the probe 309 and clamp 310.

An operation board 312 is attached to the face of the main unit 301. The operation board 312 has a power switch 313, an operation display panel 314, and a handpiece connecting section 315 for connecting the handpiece 302. One end of a connection cable 316 is coupled to the operating part 306 of the handpiece 302. A connector 317 attached to the other end of the connection cable 316 is plugged in to the handpiece connecting section 315 of the main unit 301 so that the connector 317 can be unplugged.

A handpiece 412 including an ultrasonic trocar 411 having the same components as the one in any of the aforesaid embodiments can be connected to the main unit 301 in place of the handpiece 302. A driving signal for use in generating ultrasonic vibrations can be supplied to the handpiece 412. A connection cable 414 is coupled to a grip section 413 of the handpiece 412. A connector 415 attached to an end of the connection cable 414 is plugged in to the handpiece connecting section 315 so that the connector 415 can be unplugged.

The operation display panel 314 of the main unit 301 has a setting switch (ultrasonic output setting means) for use in setting the magnitude of an ultrasonic output for normal operation for ultrasonic treatment, and a display part 319 for digitally displaying the magnitude of an ultrasonic output to be set with the setting switch 318. The setting switch 318 includes an output increase switch 318A and output decrease switch 318B for changing (increasing and decreasing) the magnitude of an ultrasonic output.

Figure 42:
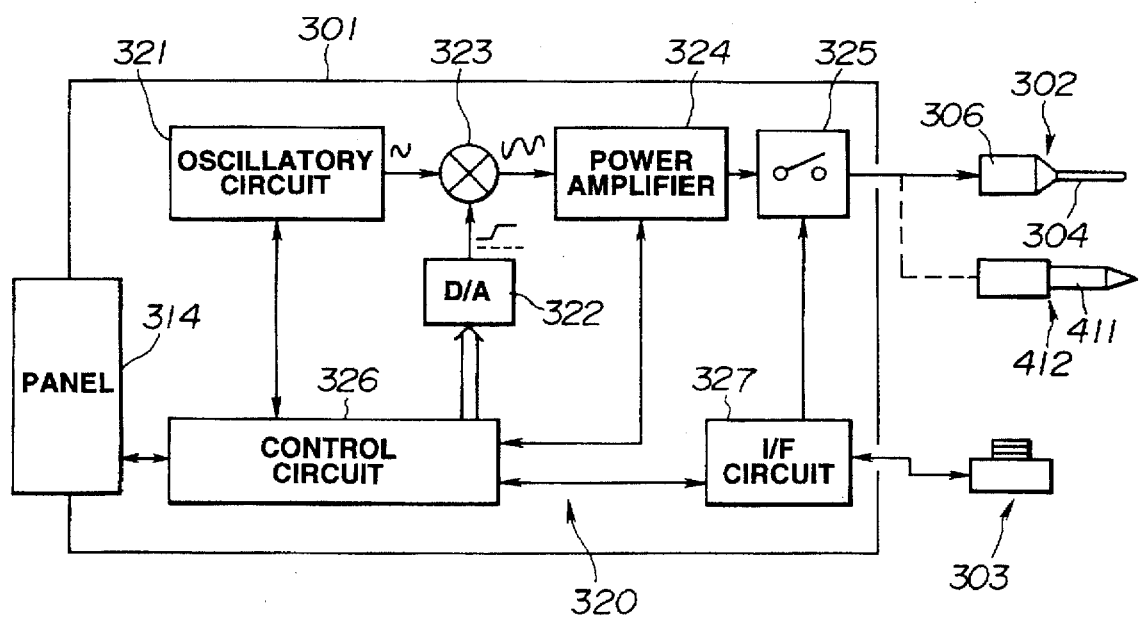
FIG. 42 is a schematic view showing the circuitry of a drive unit in the ultrasonic surgery system of the thirteenth embodiment.

A drive circuit 320 for supplying electrical energy to the ultrasonic transducer in the handpiece 302 is, as shown in FIG. 42, incorporated in the main unit 301. The drive circuit 320 consists of an oscillatory circuit 321 for generating an alternating current (ac) signal of an ultrasonic frequency, a D/A converter 322 for producing a signal indicating the magnitude of an ultrasonic output, a VCA 323 for controlling the magnitude of an ac signal produced by the oscillatory circuit 321 on the basis of a signal sent from the D/A converter 322, a power amplifier 324 for amplifying the output of the VCA 323 so as to produce power for use in driving the ultrasonic transducer in the handpiece 302, a relay 325 for making or breaking an output line of the drive circuit 320, a control circuit 326 for controlling an operation of the ultrasonic surgery system, and an interface (I/F) circuit 327 for transmitting an operation signal sent from a foot switch 303 to the control circuit 327 and relay 325.

The control unit 326 includes an operated state switching means for giving control in such a way that: when ultrasonic treatment is started by manipulating the foot switch 303, an ultrasonic output of the ultrasonic transducer in the handpiece 302 is set to a value larger than a set output value to be set with the setting switch 318; and after the ultrasonic treatment is started, when a predetermined given set time has elapsed, the ultrasonic output of the ultrasonic transducer is set to the set output value. The relay 325 in the drive circuit 320 is interposed between the handpiece connecting section 315 and power amplifier 324.

Figure 43:
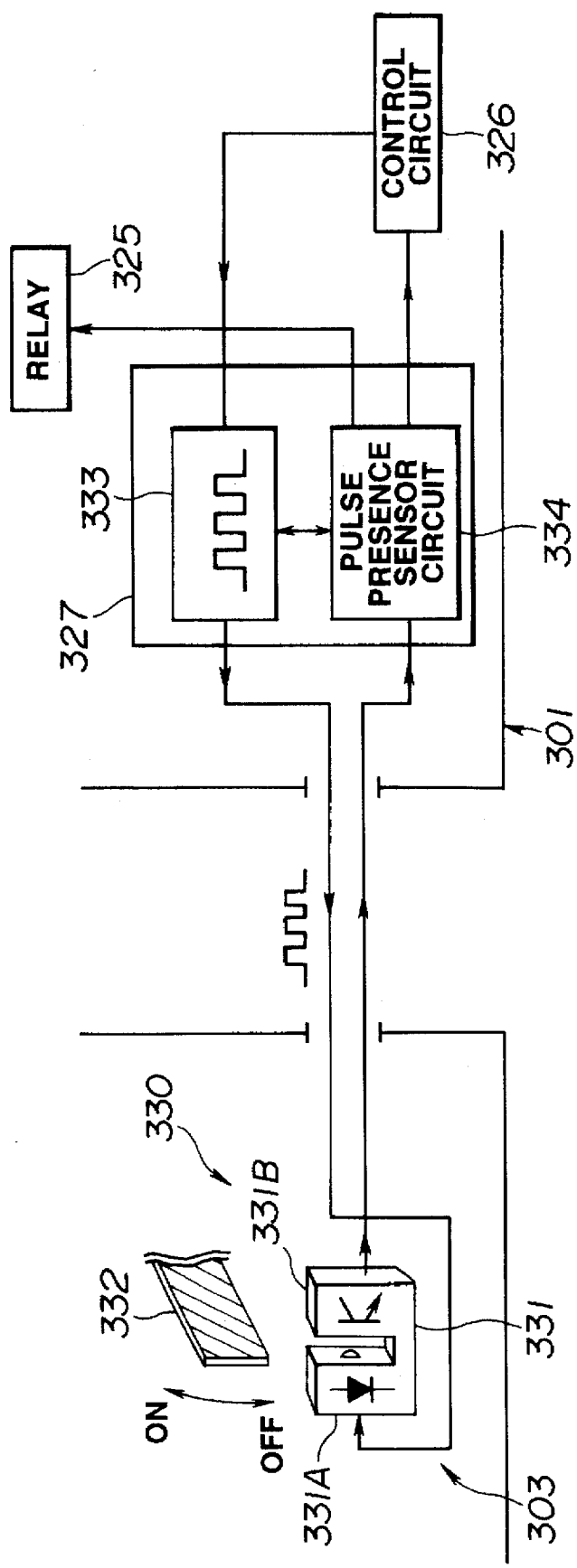
FIG. 43 is a block diagram schematically showing the mechanism of a foot switch included in the ultrasonic surgery system of the thirteenth embodiment.

The foot switch 303 includes a switch body 328 to be situated on the floor or the like, a pedal member 329 coupled to the switch body 328 so that the lower part thereof can turn freely with respect to a hinge, and a switching mechanism 330, which is shown in FIG. 43, for controlling the ON or OFF state of output of ultrasonic vibrations generated by the ultrasonic transducer according to the movement of the stepped-on pedal member 329. A constraining means, which is not shown, for retaining the pedal member 329 at a steady position to which the pedal member 329 is turned is incorporated in the switch body 328.

The switching mechanism 330 includes a photointerrupter 331 composed of a light-emitting diode 331A and light-receiving device 331B, and an interceptive plate 332 for intercepting or clearing a light path between the light-emitting diode 331A and light-receiving device 331B of the photointerrupter 331.

When the pedal member 329 of the foot switch 303 is not stepped on but retained at a standby position, the interceptive plate 332 is placed between the light-emitting diode 331A and light-receiving device 331B of the photointerrupter 331, and retained at an interceptive position at which the interceptive plate intercepts the light path in the photointerrupter 331. The interceptive plate 332 moves responsively to the manipulation of stepping on the pedal member 329 so as to clear the path between the light-emitting diode 331A and light-receiving device 331B, thus releasing the interception of the light path in the photointerrupter 331.

A pulse generator circuit 333 and pulse presence sensor circuit 334 are incorporated in the interface circuit 327 in the main unit 301. An output terminal of the pulse generator 333 is connected to the light-emitting diode 331A of the photointerrupter 331 in the foot switch 303. The pulse presence sensor circuit 334 is connected to the light-receiving device 331B of the photointerrupter 331. An input terminal of the pulse generator circuit 33 is connected to the control circuit 326. But for an instruction signal sent from the control circuit 326, a pulsating signal would not be generated.

Figure 44:
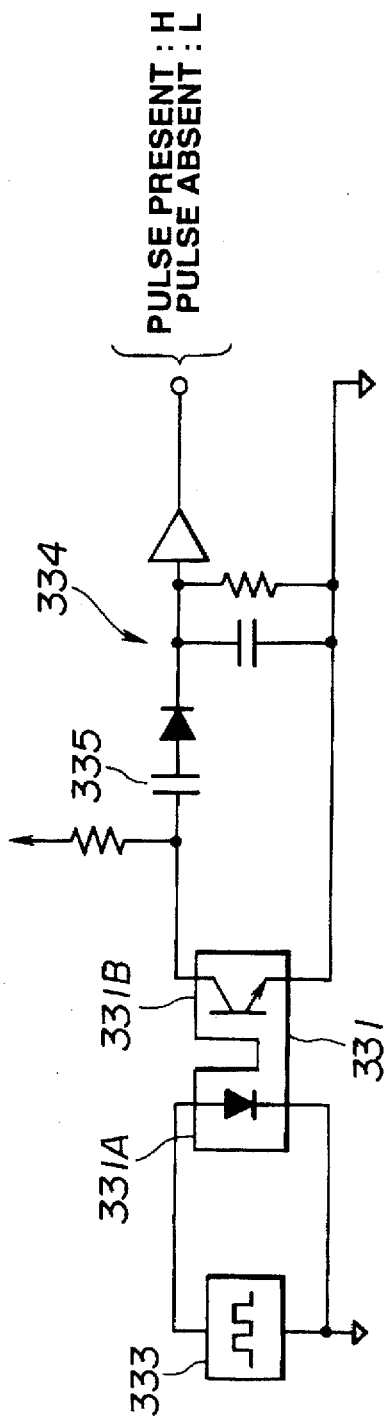
FIG. 44 is a circuit diagram showing the circuitry of a pulse presence sensor circuit included in an interface circuit shown in FIG. 43.

FIG. 44 shows the detailed circuitry of the pulse presence sensor circuit 334 in the interface circuit 327. Specifically, a capacitor 335 for cutting a direct current (dc) signal is included in the pulse presence sensor circuit 334 of this embodiment. When the pedal member 329 of the foot switch 303 is stepped on, the output of the light-receiving device 331B having received a pulsating signal from the light-emitting diode 331A of the photointerrupter 331 is received by the capacitor 335 in the pulse presence sensor circuit 334. Consequently, the dc signal is cut out and only a pulsating signal that is a high-frequency signal is allowed to pass. Thus, the pulse presence sensor circuit 334 judges whether or not a pulsating signal is present.

Next, the operation of the ultrasonic surgery system having the foregoing components will be described. When the ultrasonic surgery system of this embodiment is used as a therapeutic system, the handpiece 302 designed for treatment is connected to the main unit 301. An operator grabs the operation handle 308 of the operating part 306 of the handpiece 302 on the side of the operator's hand, and catches a living tissue, which is an object of ultrasonic treatment such as incision or coagulation, between the probe 309 and clamp 310.

In this state, when the pedal member 329 of the foot switch 303 is stepped on, ultrasonic treatment of the living tissue caught between the probe 309 and clamp 310 is carried out as described below.

First, the power switch 313 of the main unit 301 is turned on. The control circuit 326 in the main unit 301 then outputs a driving signal to the pulse generator circuit 333 in the interface circuit 327, whereby the pulse generator circuit 333 is driven. When the pulse generator circuit 333 is driven, it generates a pulsating signal. With this signal, the light-emitting diode 331A of the photointerrupter 331 emits pulsed light.

In this state, when the pedal member 329 of the foot switch 303 is stepped on, the output of the main unit 301 of the ultrasonic surgery system is turned ON or OFF. In other words, in a standby state in which the foot switch 303 is not stepped on, the interceptive plate 332 is retained at the interceptive position at which the light path between the light-emitting diode 331A and light-receiving device 331B of the photointerrupter 331 is intercepted by the interceptive plate 332. In this case, a light signal is not transmitted to the light-receiving device 331B of the photointerrupter 331. A low-level signal of a certain level is output from the light-receiving device 331B.

The low-level signal that is the output signal of the light-receiving device 331B at that time is input to the pulse presence sensor circuit 334 in the interface circuit 327. When the low-level signal of a certain level is input, it is judged that the foot switch 303 is OFF or faulty. Ultrasound output is retained OFF.

When the operator steps on the pedal member 329 of the foot switch 303, the interceptive plate 332 moves responsively to the movement of the stepped-on pedal member 329. The interception of the light path in the photointerrupter 331 is released. A pulsed light signal produced by the light-emitting diode 331A is then transmitted to the light-receiving device 331B of the photointerrupter 331. A pulsating signal is output from the light-receiving device 331B.

The output signal (pulsating signal) sent from the light-receiving device 331B at that time is input to the pulse presence sensor circuit 334 in the interface circuit 327. When the pulsating signal is input, the pulse presence sensor circuit 334 judges that the foot switch 303 is normal and turned ON. In this case, a Pulse Sensed signal is output from the pulse presence sensor circuit 334 to the control circuit 326 and relay 325. In other words, when the stepped-on state of the pedal member 329 is reported to the control circuit 326 via the interface circuit 327, the relay 325 is turned ON only while the foot switch 303 is being ON.

When the Pulse Sensed signal sent from the pulse presence sensor circuit 334 is input to the control circuit 326, the control circuit 326 outputs a driving signal to the oscillatory circuit 321. The oscillatory circuit 321 is then driven. At this time, the control circuit 326 sends data, which represents a level corresponding to the magnitude of an output set with the setting switch 318 on the operation display panel 314, to the D/A converter 322. Based on the data, the D/A converter 322 controls the operation of the VCA 323. When an alternating current (ac) signal of an ultrasonic frequency generated by the oscillatory circuit 321 is input to the VCA 323, the VCA 323 produces a signal of the ultrasonic frequency having a desired magnitude.

Furthermore, the ultrasonic signal is sent to and amplified by the power amplifier 324. The power is then supplied to the ultrasonic transducer in the handpiece 302 via the relay 325. The ultrasonic transducer in the handpiece 302 is then driven, thus causing the probe 309 to vibrate at the ultrasonic frequency. Consequently, the living tissue caught between the probe 309 and clamp 310 is cut or coagulated due to fast friction. The ultrasonic treatment of the living tissue is thus achieved.

Furthermore, when desired ultrasonic treatment is completed, the manipulation of stepping on the pedal member 329 of the foot switch 303 is ceased. When the manipulation of stepping on the pedal member 329 of the foot switch 303 is thus ceased, the light path between the light-emitting diode 331A and light-receiving device 331B of the photointerrupter 331 is intercepted by the interceptive plate 332 responsively to the return movement of the pedal member 329. In this case, therefore, no light signal is transmitted to the light-receiving device 331B. A low-level signal of a certain level is output from the light-receiving device 331B.

When the photointerrupter 331 fails, or when the light-emitting diode 331A does not glow or the light-receiving device 331B fails to receive light, though the light path in the photointerrupter 331 is not intercepted by the interceptive plate 332, a low-level or high-level signal of a certain level is output.

When the low-level signal of a certain level output from the light-receiving device 331B is sent to the pulse presence sensor circuit 334 in the interface circuit 327, the pulse presence sensor circuit 334 judges that the foot switch 303 is normal and turned OFF, or faulty. In this case, control is given so that ultrasound output can be turned OFF. The ultrasound output is then ceased. Thereafter, the therapeutic part 305 of the handpiece 302 is moved to the location of a living tissue that is an object of the next ultrasonic treatment. The same manipulation as the foregoing one is then performed on the living tissue to be treated next.

When the ultrasonic surgery system of this embodiment is used as a trocar system, the handpiece 412 including the ultrasonic trocar 411 is connected to the main unit 301. An operator grabs the grip section 413 and abuts the trocar against a region to be punctured. In this state, the foot switch 303 is manipulated in the same manner as that described previously, whereby ultrasonic driving power provided by the drive circuit 320 is supplied to the ultrasonic transducer in the handpiece 412. This causes the obturator in the ultrasonic trocar 411 to vibrate at an ultrasonic frequency. With the ultrasonic vibrations, fast friction occurs at the region against which the obturator is abutted, and a living tissue is cut. Consequently, the tip of the obturator can be thrust into the abdominal wall readily.

For operating the main unit 301 of the ultrasonic surgery system, the setting switch 318 on the operation display panel 314 of the main unit 301 is manipulated in advance in order to set the magnitude of ultrasound output for normal operation during which ultrasonic treatment is carried out.

For ultrasonic treatment such as resection, coagulation, or puncture using a trocar, the magnitude of ultrasound output from the ultrasonic transducer in the handpiece 302 or 412 is controlled by the control circuit 326 as described below. That is to say, when ultrasonic treatment is started by manipulating the foot switch 303, the ultrasonic transducer in the handpiece 302 or 412 is driven with the ultrasonic output from the ultrasonic transducer set to a value larger than a set output value to be set with the setting switch 318.

After ultrasonic treatment is started, when a predetermined given set time has elapsed, the magnitude of the ultrasound output from the ultrasonic transducer is controlled to be set to the set output value.

Figure 46:
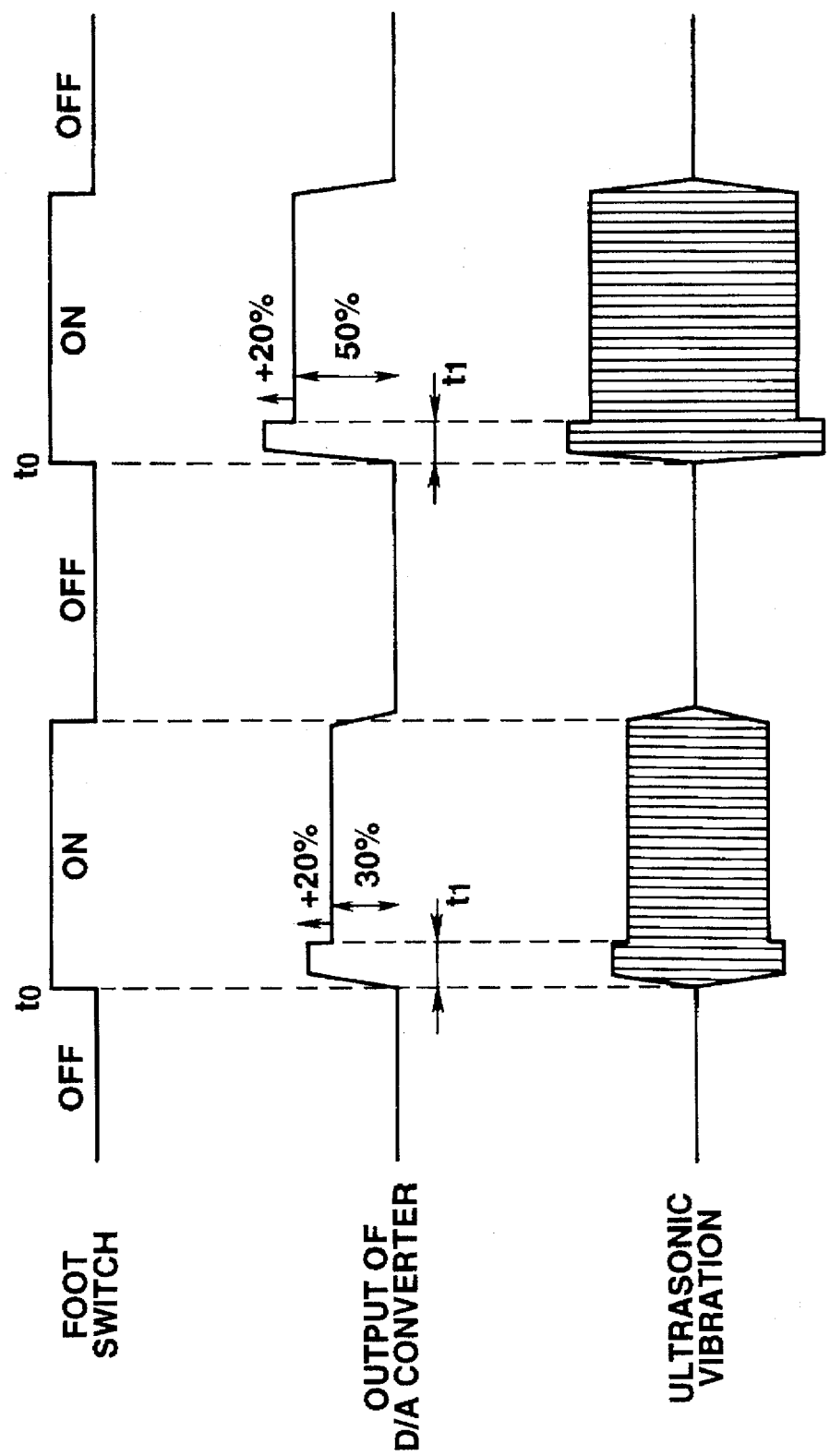
FIG. 46 is a characteristic chart for explaining an ultrasonic output control operation in the ultrasonic surgery system of the thirteenth embodiment.

FIG. 46 shows an example of a state in which the magnitude of ultrasound output from the ultrasonic transducer in the handpiece 302 or 412 included in the ultrasonic surgery system is controlled for ultrasonic treatment. When output of ultrasound from the ultrasonic transducer in the handpiece 302 or 412 during normal operation is set to, for example, 30% with the setting switch 318, control is given so that the output of ultrasound can be set to a value (for example, larger by 20%) bit larger than the set value 30% for the first t1 sec. since time instant t0 at which ultrasonic treatment is started by stepping on the pedal member 329 of the foot switch 303.

Furthermore, after ultrasonic treatment is started, when t1 sec. has elapsed, the operative state of the system is changed to give control so that output of ultrasound can be set to the set value for normal operation which is set with the setting switch 318, that is, 30%.

Even when a set value of ultrasound output for normal operation which is set with the setting switch 318 is, for example, 50%, control is given so that the ultrasound output can be set to a value bit larger (for example, larger by 20%) than the set value 50% for the first t1 sec. since time instant t0 at which ultrasonic treatment is started.

Even in this case, after the ultrasonic treatment is started, when t1 sec. has elapsed, the operative state of the system is changed to give control so that the ultrasound output can be set to the set value for normal operation which is set with the setting switch 318, that is, 50%.

Control of ultrasound output is realized by manipulating data to be sent from the control circuit 326 to the D/A converter 322. Specifically, when a signal for manipulating ultrasound output is input to the control circuit 326 via the interface circuit 327, first, data representing a product of a set value, which is set with the setting switch 318, by a certain constant (for example, 1.2) is produced. After ultrasonic treatment is started, the data is sent to the D/A converter 322 for t1 sec. (for example several hundreds msec.). Based on the data, the D/A converter 322 controls the operation of the VCA 323. When an ac signal of an ultrasonic frequency generated by the oscillatory circuit 321 is input to the VCA 323, the VCA 323 produces a signal of the ultrasonic frequency having a magnitude corresponding to the product of the set value, which is set with the setting switch 318, by the certain constant.

When t1 sec. has elapsed since time instant t0 at which ultrasonic treatment is started, switching is carried out so that data representing the set value for normal operation, which is set with the setting switch 318, can be sent from the control circuit 326 to the D/A converter 322. Thus, ultrasound output is controlled according to the set value for normal operation.

The foregoing circuitry exerts the advantage described below. That is to say, when ultrasonic treatment is started by manipulating the foot switch 303, the ultrasonic transducer in the handpiece 302 or 412 is driven with ultrasound output from the ultrasonic transducer set to a value larger than the set output value for normal operation which is set with the setting switch 318. After the ultrasonic treatment is started, when a predetermined given setting time has elapsed, control is given so that the ultrasound output from the ultrasonic transducer can be set to the set output value. In the initial stage immediately after the foot switch 303 is manipulated, a high-power ultrasonic output can be provided for a short period of time. This results in the advantage of the improved response of ultrasonic treatment based on ultrasonic vibrations, such as, incision, coagulation, or puncture using a trocar.

Since a pulsating signal is adopted for the photointerrupter 331 of the switching mechanism 330 in the foot switch 303, even if the photointerrupter 331 fails, there is not the fear that the signal sent from the photointerrupter 331 is continued to be output. Moreover, since the output line can be disconnected forcibly, if the photointerrupter 331 fails, ultrasound output can be inhibited reliably.

The pulse presence sensor circuit 334 outputs a signal for controlling the relay 325 that makes or breaks the output line of the drive circuit 320 in the main unit 301. While the foot switch 303 is being ON, the relay 325 is closed so that the output signal of the drive circuit 320 can be sent to the ultrasonic transducer. If the foot switch 303 is OFF or faulty, supply of energy to the ultrasonic transducer in the handpiece 302 can be prevented reliably.

If any abnormality occurs in the control circuit 326, a pulsating signal is not generated. Output of a signal from the photointerrupter 331 can therefore be inhibited reliably. This results in improved safety.

Figure 45:
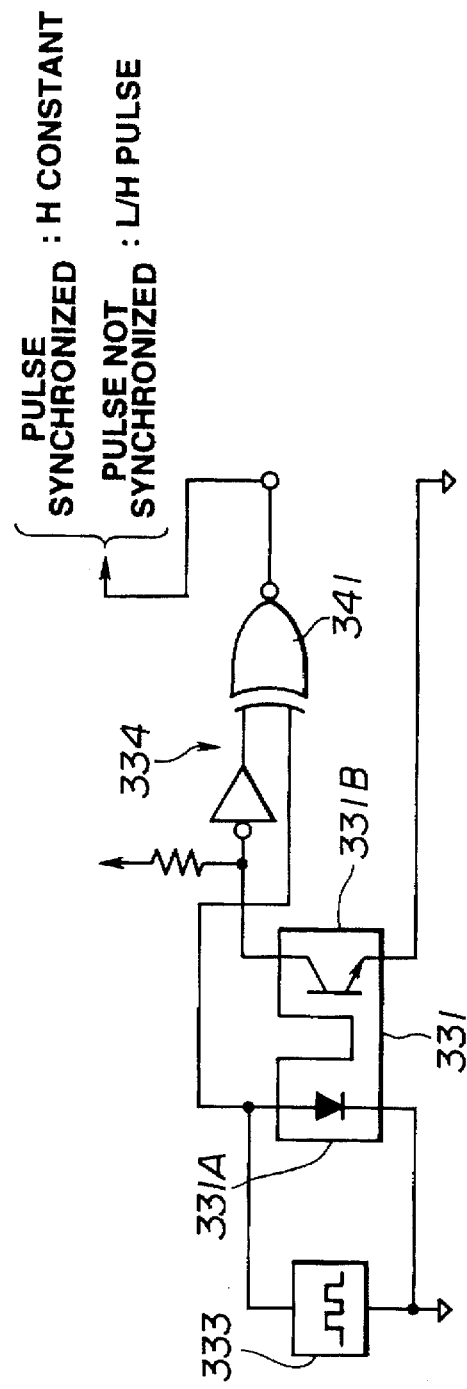
FIG. 45 is a circuit diagram showing the circuitry of a variant of the pulse presence sensor circuit included in the interface circuit shown in FIG. 43.

FIG. 45 shows a variant of the pulse presence sensor circuit 334 in the thirteenth embodiment. A pulse presence sensor circuit 334 of this variant includes an exclusive-OR circuit 341. When the pedal member 329 of the foot switch 303 is stepped on, an output sent from the light-receiving device 331B having received a pulsating signal from the light-emitting diode 331A of the photointerrupter 331, and a pulsating signal causing the light-emitting diode 331A to emit pulsed light are input to the exclusive-OR circuit 341. At this time, while the light-receiving device 331B is receiving pulses, a synchronized pulsating signal is input to the exclusive-OR circuit 341 through an input terminal thereof. The output of the exclusive-OR circuit is high and constant.

During a period during which the light-receiving element 331B does not receive any pulse, the output of the exclusive-OR circuit 341 varies in a pulsed manner. The control circuit 326 may check the signal to see if the foot switch 303 is ON or OFF. Alternatively, as shown in FIG. 44, a capacitor may be used to sense the presence of an alternating current.

Figure 47:
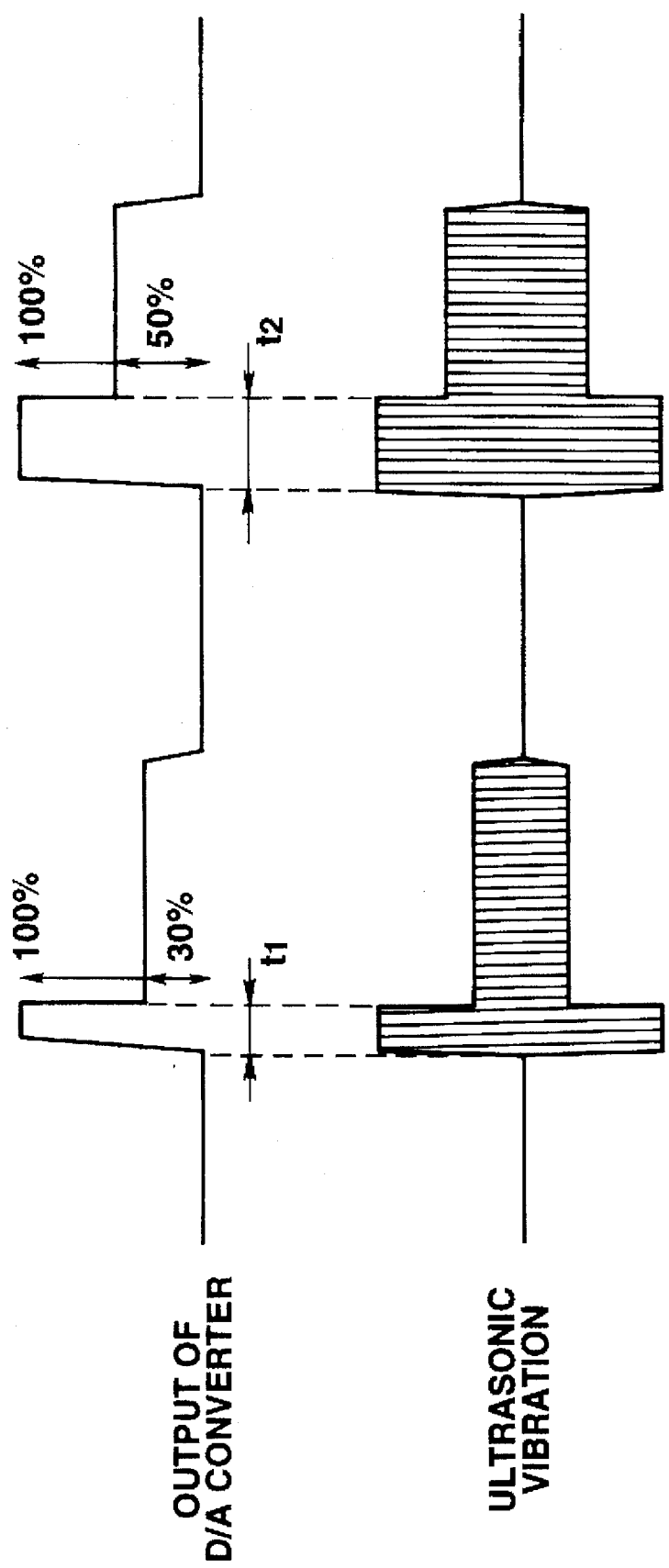
FIG. 47 is a characteristic chart showing a variant of the ultrasonic output control operation in the ultrasonic surgery system of the thirteenth embodiment.

FIG. 47 shows a variant of ultrasound output control in the ultrasonic surgery system of the thirteenth embodiment. In this variant, output of ultrasound from the ultrasonic transducer in the handpiece 302 or 412 during normal operation, which is set with the setting switch 318, is set to, for example, 30%, control is given so that ultrasound can be output 100% for the first t1 sec. since time instant t0 at which ultrasonic treatment is started by stepping on the pedal member 329 of the foot switch 303.

After ultrasonic treatment is started, when t1 sec. has elapsed, the operative state of the system is changed to give control so that the ultrasound output can be changed back to the set value for normal operation which is set with the setting switch 318, that is, 30%.

If the set value of ultrasound output for normal operation which is set with the setting switch 318 is, for example, 50%, control is given so that ultrasound can be output 100% for the first t2 sec. since time instant t0 at which ultrasonic treatment is started.

Even in this case, after ultrasonic treatment is started, when t2 sec. has elapsed, the operative state is changed to give control so that ultrasound output can be changed back to the set value for normal operation which is set with the setting switch 318, that is, 50%.

In this variant, time t1 is longer than time t2. However, the relationship between the times t1 and t2 is not limited to this one. Moreover, the percentage of ultrasound output to be set immediately after the start of ultrasonic treatment may not be 100%. Furthermore, the foregoing circuitry can be adapted to constant current drive control for controlling the amplitude of ultrasonic vibrations in so that the amplitude thereof can remain constant.

Figure 48:
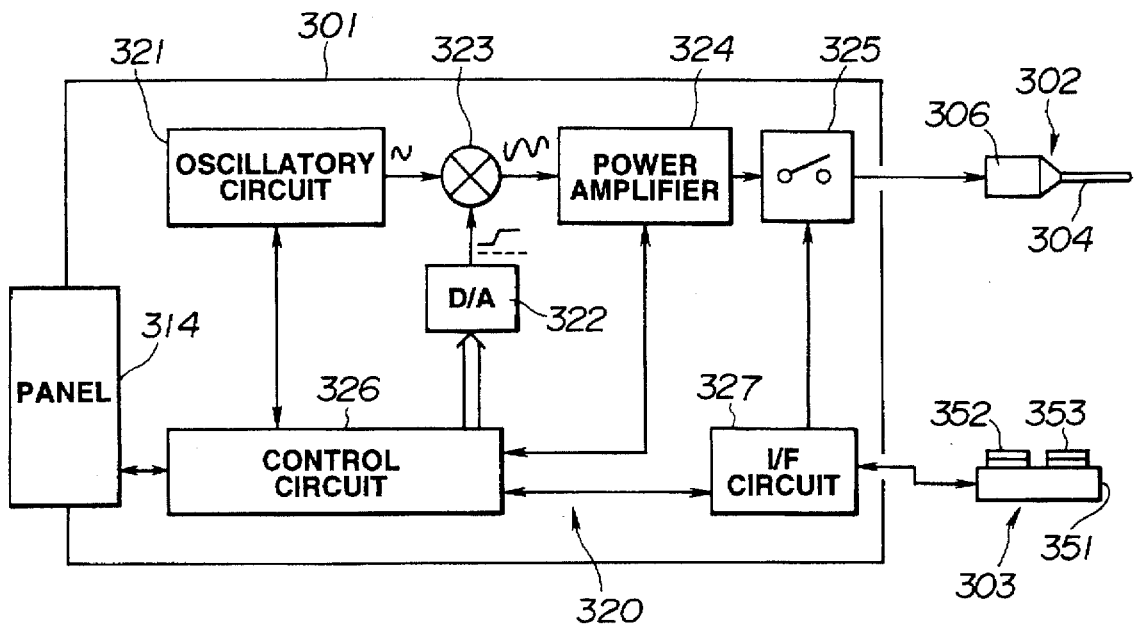
FIG. 48 is a block diagram schematically showing the configuration of an ultrasonic surgery system in accordance with the fourteenth embodiment of the present invention.
Figure 49:
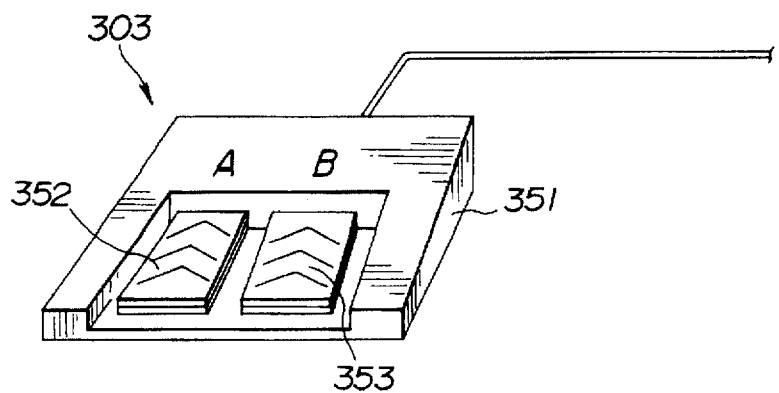
FIG. 49 is an oblique view showing the appearance of a foot switch in the fourteenth embodiment.
Figure 50:
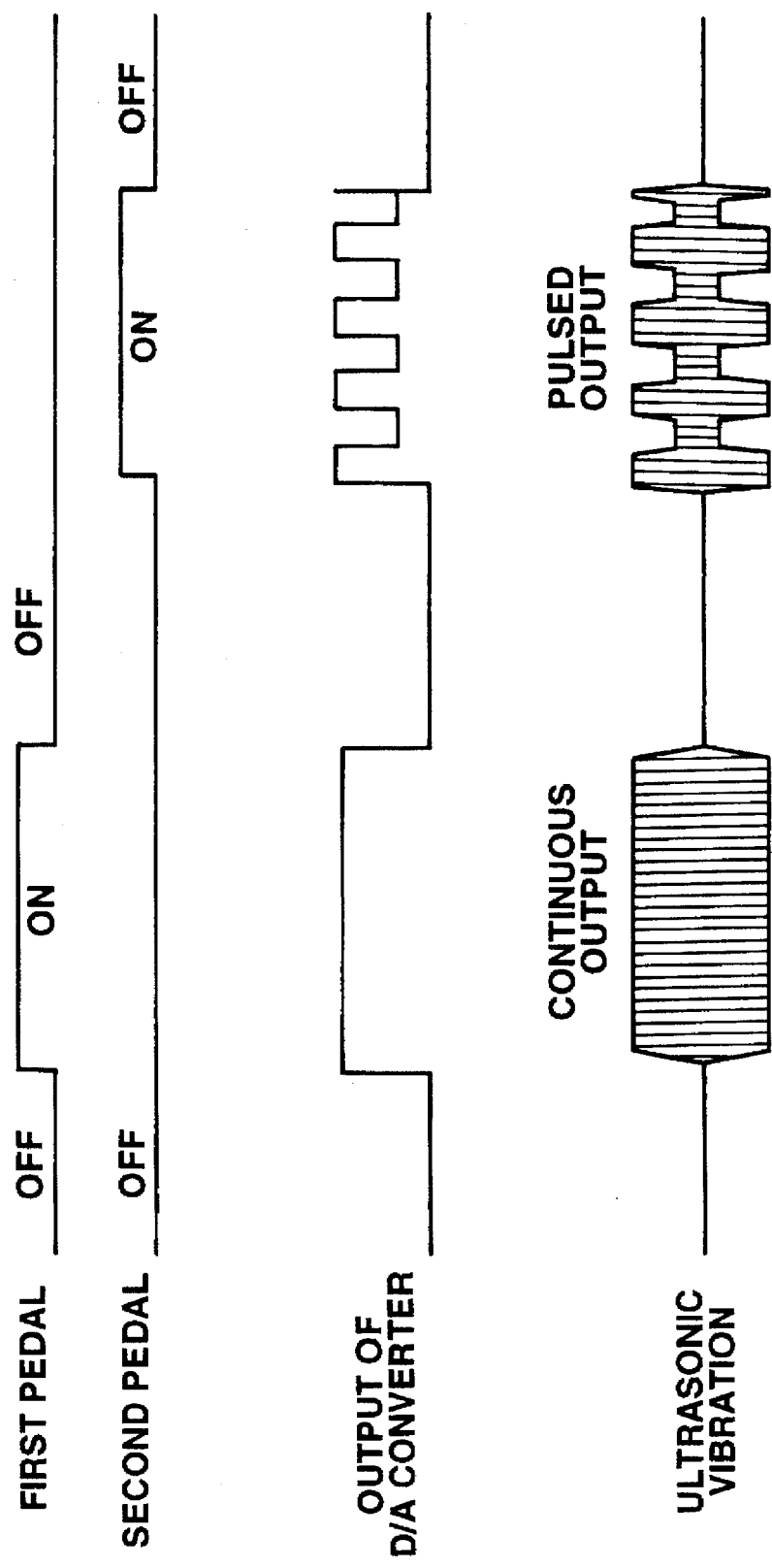
FIG. 50 is a characteristic chart for explaining an ultrasonic output control operation in the ultrasonic surgery system of the fourteenth embodiment.

FIGS. 48 to 50 show the fourteenth embodiment of the present invention. In this embodiment, the structure of the foot switch 303 included in the ultrasonic surgery system of the thirteenth embodiment has been changed as described below.

A foot switch 303 in this embodiment shown in FIGS. 48 and 49 has a double switching mechanism in which a switch body 351 to be situated on the floor or the like has two operation pedals 352 and 353, which operate independently, juxtaposed. In this case, one of the operation pedals that is the first operation pedal 352 is designed to act as an operation switch for outputting continuous ultrasonic vibrations, while the other second operation pedal 353 is designed to act as an operation switch for outputting pulsed ultrasonic vibrations.

Next, the operation of this embodiment having the foregoing configuration will be described. FIG. 50 shows an example of a state in which the magnitude of ultrasound output from the ultrasonic transducer in the handpiece 302 included in the ultrasonic surgery system of this embodiment for ultrasonic treatment is controlled.

In this embodiment, when the first operation pedal 352 of the foot switch 303 is stepped on, the interface circuit 327 notifies the control circuit 326 of the state. At the same time, the relay 325 is turned ON. The control circuit 326 sends data, of which signal level is associated with the magnitude of output set with the setting switch 318 on the operation display panel 314, to the D/A converter 322. Based on the data, the D/A converter 322 controls the operation of the VCA 323. When an ac signal of an ultrasonic frequency generated by the oscillatory circuit 321 is input to the VCA 323, the VCA 323 produces a signal of the ultrasonic frequency having a desired magnitude.

When the first operation pedal 352 is stepped on, output of ultrasonic vibrations is continuous vibrational output. After the handpiece 302 for treatment is connected, when ultrasonic treatment is started, fast friction occurs intermittently between the probe 309 of the handpiece 302 and a living tissue. The living tissue is resected while being coagulated.

When the second operation pedal 353 of the foot switch 303 is stepped on, the control circuit 326 sends a signal, of which level is associated with the magnitude of output set with the setting switch 318 on the operation display panel 314, and a signal, of which level is associated with a smaller magnitude and which has a lower amplitude, alternately to the D/A converter 322.

When the second operation pedal 353 is manipulated, vibrational output of ultrasonic vibrations is intermittent. When ultrasonic vibrations are propagated from the probe 309 of the handpiece 302 to a living tissue, the living tissue is not resected but merely coagulated.

Since the percentage of ultrasound output is set with the setting switch 318 on the operation display panel 324, when the peak value alone is changed with the low level of a pulsating output unchanged, a level or speed of coagulating a living tissue can be adjusted.

The aforesaid configuration has the advantage described below. That is to say, the double switching mechanism in which the two operation pedals 352 and 353 are juxtaposed on the switch body 351 of the foot switch 303, the first operation pedal 352 acts as an operation switch for outputting continuous ultrasonic vibrations, and the second operation pedal 353 acts as an operation switch for outputting pulsed ultrasonic vibrations. Owing to this structure, when the first operation pedal 352 is stepped on, a living tissue can be resected by the probe 309 of the handpiece 302. When the second operation pedal 353 is stepped on, a living tissue can be coagulated by the probe 309 of the handpiece 302.

By selectively utilizing the two operation pedals 352 and 353 on the switch body 351, the common probe 309 of the handpiece 302 can be used for either incision of a living tissue by means of ultrasonic vibrations or coagulated thereof by means of ultrasonic vibrations. This makes it possible to omit such annoying work as, for example, changing a distal chip to be attached to the distal end of the probe 309 of the handpiece 302 from a distal chip designed for incising a living tissue to a distal chip designed for coagulation or vice versa. Consequently, the maneuverability of the handpiece 302 can be improved.

In this embodiment, a method for outputting ultrasonic vibrations in a pulsed manner is realized by manipulating an output of the D/A converter. Alternatively, a set control value to be set in a constant current drive circuit employed in driving an ultrasonic transducer may be varied in a pulsed manner. Otherwise, an electrical circuit for producing a pulsating signal may be included.

Figure 51:
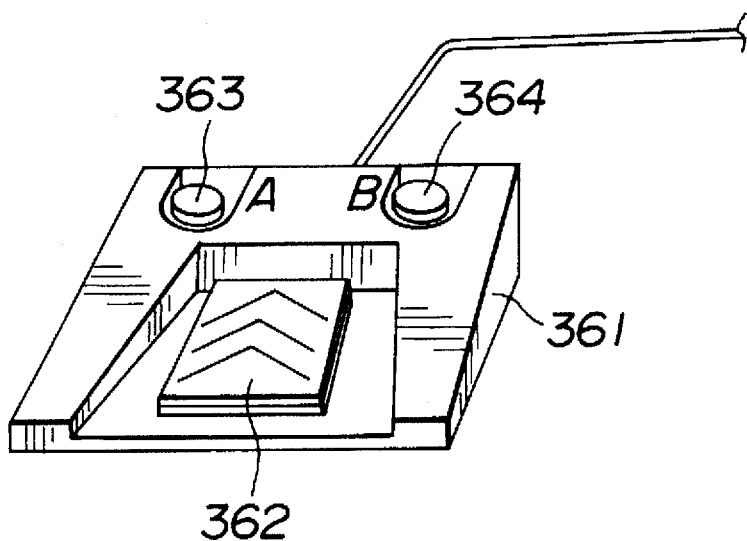
FIG. 51 is an oblique view showing the appearance of a foot switch in accordance with the fifteenth embodiment of the present invention.

FIG. 51 shows the fifteenth embodiment of the present invention. In this embodiment, the structure of the foot switch 303 included in the ultrasonic surgery system of the thirteenth embodiment has been modified as described below.

Specifically, a foot switch 303 of this embodiment has a switching mechanism in which one main pedal 362 and two sub-pedals 363 and 364 for selecting incision of a living tissue by means of ultrasonic vibrations or coagulation thereof by means of ultrasonic vibrations are located on a switch body 361 to be situated on the floor or the like. In this case, before an operator manipulates the main pedal 362, he/she manipulates either of the two sub-pedals 363 and 364 so as to select incision or coagulation, and then uses the main pedal 362 to start ultrasound output.

In this embodiment, for example, when one of the sub-pedals or the sub-pedal 363 is selected, if the main pedal 362 is stepped on, the probe 309 of the handpiece 302 resects a living tissue. When the other sub-pedal 364 is selected, if the main pedal 362 is stepped on, the probe 309 of the handpiece 302 coagulates a living tissue.

After either of the two sub-pedals 363 and 364 is used to select the function of incising a living tissue or the function of coagulating it, when the main pedal 362 is manipulated, the probe 309 of the common handpiece 302 can be used to incise or coagulate the living tissue by means of ultrasonic vibrations. Even this embodiment can provide the same advantage as the fourteenth embodiment (See FIGS. 48 to 50).

The two sub-pedals 363 and 364 for use in selecting incision of a living tissue by means of ultrasonic vibrations or coagulation thereof by means of ultrasonic vibrations may be located on the handpiece 302. In either case, it is important that an operator can readily select incision or coagulation as a therapeutic function for a living tissue based on ultrasonic vibrations.

Figure 52:
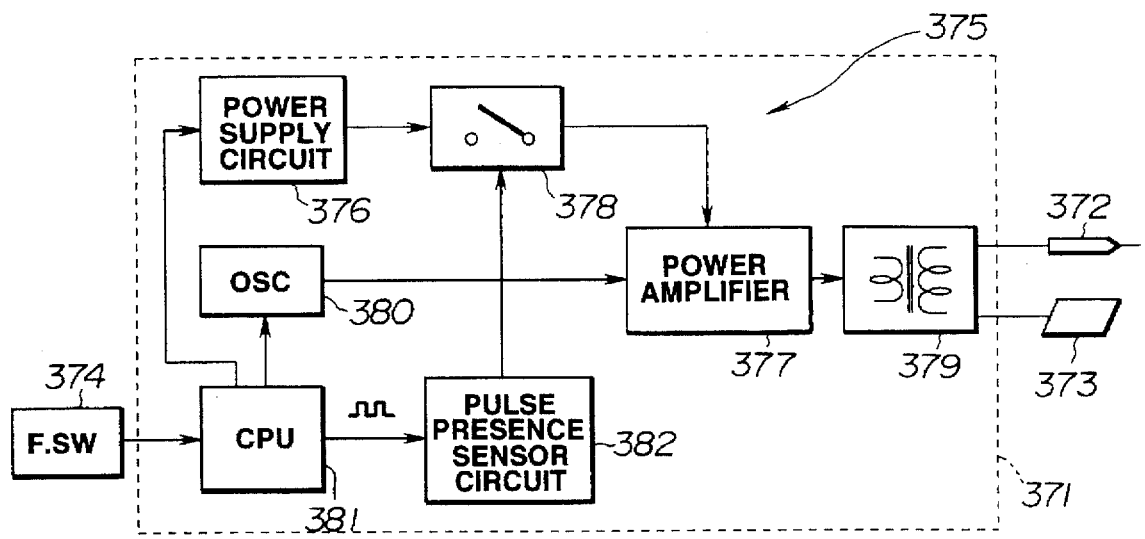
FIG. 52 is a block diagram schematically showing the configuration of an ultrasonic surgery system in accordance with the sixteenth embodiment of the present invention.

FIG. 52 shows the sixteenth embodiment of the present invention. This embodiment includes a safety function for preventing malfunction is incorporated in a cautery knife. A cautery knife handpiece 372, a counter-electrode plate 373, and a foot switch (switching means ) 374 for turning ON or OFF output are connected to a main unit (drive unit) 371 for a cautery knife in accordance with this embodiment.

Furthermore, a drive circuit 375 for the cautery knife is incorporated in a main unit 371. The drive circuit 375 includes a power supply circuit 376 for outputting a voltage proportional to an output of the cautery knife, a power amplifier 377 for producing a high-frequency output, a relay 378 for making or breaking a current path for conveying a voltage from the power supply circuit 376 to the power amplifier 377, an output transformer 379 for insulating and boosting an output of the power amplifier 377, an oscillatory circuit 380 for oscillating a high-frequency signal, a microcomputer (CPU) 381 for controlling the whole cautery knife, and a pulse presence sensor circuit 382 for controlling the relay 378 by sensing whether or not a pulsating signal sent from the CPU 381 is present.

Next, the operation of the embodiment having the foregoing components will be described. When the cautery knife is used, if the foot switch 374 is stepped on, the signal is transmitted to the CPU 381. The CPU 381 outputs a pulsating signal when operating normally. When the CPU 381 outputs a pulsating signal, the pulse presence sensor circuit 382 turns ON the relay 378. In this case, power is supplied to the power amplifier 377 in order to produce an output for the cautery knife.

If the CPU 381 should operate abnormally, although the foot switch 374 has been stepped on, a pulsating signal would not be output. The relay 378 is therefore not turned ON. Consequently, no cautery knife output is produced.

In this embodiment, since the CPU 381 incorporated in the drive circuit 375 for the cautery knife generates a pulsating signal, if the CPU 381 should run abnormally, output of the pulsating signal would be suspended in order to disable the foot switch 374 (a watchdog).

Figure 53:
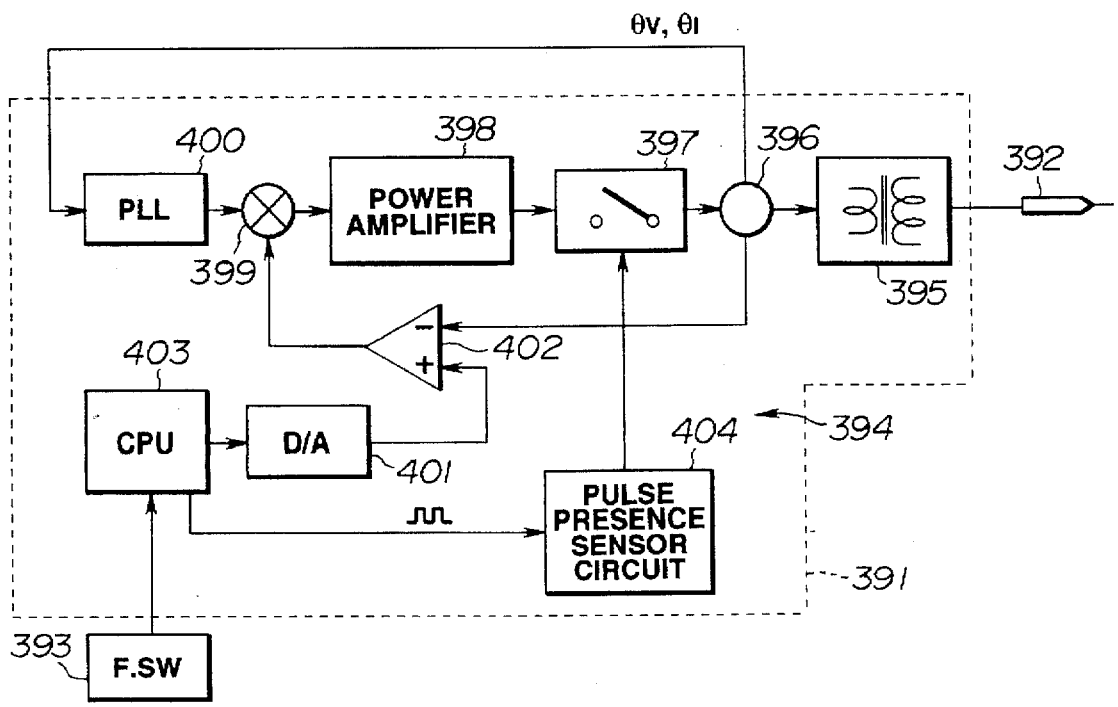
FIG. 53 is a block diagram schematically showing the configuration of an ultrasonic surgery system in accordance with the seventeenth embodiment of the present invention.

FIG. 53 shows the seventeenth embodiment of the present invention. In this embodiment, an ultrasonic transducer drive circuit 394 adopting a PLL control system as a resonance tracking system and a constant current control system as an amplitude control system is incorporated in an ultrasonic surgery system.

A handpiece 392 with a built-in ultrasonic transducer and a foot switch (switching means) 393 for turning ON or OFF ultrasound output are connected to a main unit (drive unit) 391 of the ultrasonic surgery system of this embodiment.

Moreover, the ultrasonic transducer drive circuit 394 is incorporated in the main unit 391. The drive circuit 394 includes a constant current loop composed of an output transformer 395 for insulation and boosting, a voltage/current detection circuit 396 for detecting a voltage and current, a relay 397 for making or breaking an output line, a power amplifier 398, a voltage control amplifier 399, a phase-locked loop (PLL) 400 for tracking a resonance on the basis of a voltage phase signal and current phase signal sent from the voltage/current detection circuit 396, a D/A converter 401 for setting the magnitude of ultrasound output, a differential amplifier 402 for comparing a signal representing the magnitude of a current sent from the voltage/current detection circuit 396 with a signal sent from the D/A converter 401. The drive circuit 394 further includes a microcomputer (CPU) 403 for controlling a whole ultrasonic surgery system, and a pulse presence sensor circuit 404 for controlling the relay 397 by sensing whether or not a pulsating signal sent from the CPU 403 is present.

Next, the operation of this embodiment having the foregoing components will be described. When the foot switch 393 is stepped on during maneuver of the ultrasonic surgery system, the signal is transmitted to the CPU 403. The CPU 403 outputs a pulsating signal when operating normally. When the CPU 403 outputs a pulsating signal, the pulse presence sensor circuit 404 turns ON the relay 397. In this case, an output signal from the power amplifier 398 is transmitted to the output transformer 395 via the relay 497 and voltage/current detection circuit 396. The ultrasonic transducer in the handpiece 392 is then driven, whereby ultrasound output is started.

If the CPU 403 should be abnormal, although the foot switch 393 has been stepped on, no pulsating signal would be output. The relay 397 is therefore not turned ON, and no ultrasound is output from the handpiece 392.

In this embodiment, since the CPU 403 incorporated in the ultrasonic transducer drive circuit 394 generates a pulsating signal, the same advantage as that of the sixteenth embodiment (See FIG. 52) can be provided.

In the present invention, it will be apparent that a wide range of different embodiments can be constituted on the basis of the invention without the departure from the spirit and scope of the invention. This invention will be limited to the accompanying claims but not restricted to any specific embodiment.

What is claimed is:

1. An ultrasonic trocar system, comprising:
   a cannula having a guide bore;
   an obturator to be passed through said guide bore of said cannula so that the obturator can be removed; and
   a vibration generating means for generating ultrasonic vibrations to be propagated to said obturator,
   wherein said obturator is vibrated at an ultrasonic frequency to puncture a somatic layer,
   wherein an intermediate member is interposed between said cannula and said obturator, and
   wherein said intermediate member is a tapered member whose distal part has a taper surface that is tapered in the same direction as a direction in which a distal part of said obturator is tapered.

2. An ultrasonic trocar system according to claim 1, wherein said intermediate member is made of a material whose acoustic impedance is different from those of materials forming said cannula and said obturator.

3. An ultrasonic trocar system according to claim 1, wherein said intermediate member is arranged to be acoustically separated from said cannula and obturator.

4. An ultrasonic trocar system according to claim 1, wherein said intermediate member is a member at least whose distal part has a surface with a low coefficient of friction and which is made of a material having low thermal conductivity.

5. An ultrasonic trocar system according to claim 1, wherein said obturator has a tip thereof shaped sharply.

6. An ultrasonic trocar system according to claim 1, wherein an annular member having a slide-enabling property is located on an outer circumference of the distal part of said obturator.

7. An ultrasonic trocar system according to claim 1, wherein said obturator is formed with a member having a space therein.

8. An ultrasonic trocar system according to claim 7, wherein said obturator has an object which has an acoustic impedance different from an outer surface member of said obturator placed in said space.

9. An ultrasonic trocar system, comprising:
   a cannula having a guide bore;
   an obturator to be passed through said guide bore of said cannula so that the obturator can be removed; said obturator having a distal part; and
   a vibration generating means for generating ultrasonic vibrations to be propagated to said obturator,
   wherein said obturator is vibrated at an ultrasonic frequency to puncture a somatic layer,
   wherein an intermediate member is interposed between said cannula and said obturator, and
   wherein an annular member having a slide-enabling property is located on an inner circumference of the distal part of said intermediate member.

10. An ultrasonic trocar system comprising:
    a cannula having a guide bore;
    an obturator to be passed through said guide bore of said cannula so that the obturator can be removed; and
    a vibration generating means for generating ultrasonic vibrations to be propagated to said obturator,
    wherein said obturator is vibrated at an ultrasonic frequency to puncture a somatic layer,
    wherein an intermediate member is interposed between said cannula and said obturator, and
    wherein said obturator has a distal part thereof shaped substantially like a cone, and the conical part has grooves, which are intended to reduce a contact area, formed on a surface thereof.

11. An ultrasonic trocar system according to one of claim 1, 4, or 10, further comprising a vibration control means for providing control so that vibration energy whose level is equal to or larger than a permissible level cannot be propagated from a portion of the distal part of said obturator in contact with a living body to the living body.

12. An ultrasonic trocar system according to claim 11, wherein said vibration control means includes a constant amplitude driving means for driving said obturator at a constant amplitude, a load display/notification means for displaying and notifying the situation of a load on said obturator, and a switch means capable of turning ON or OFF vibration of said obturator.

13. An ultrasonic trocar system according to claim 11, wherein said vibration control means includes a drive control means for giving pulsed vibrations of a small repetition frequency to said obturator.

14. An ultrasonic trocar system, comprising:
    an obturator adapted to be vibrated at an ultrasonic frequency to puncture a somatic layer;
    a plurality of kinds of cannulas having guide bores into which said obturator can be inserted and having different diameters; and
    a plurality of kinds of intermediate members, each interposed between a cannula and said obturator, having inner diameters matching the outer diameter of said obturator and outer diameters matching the different inner diameters of said cannulas.

15. An ultrasonic trocar system, comprising:
    an obturator adapted to be vibrated at an ultrasonic frequency to puncture a somatic layer;
    a plurality of kinds of cannulas having guide bores into which said obturator can be inserted and having different diameters;
    a plurality of kinds of intermediate members, each interposed between a cannula and said obturator, having inner diameters matching the outer diameter of said obturator and outer diameters matching the different inner diameters of said cannulas;
    an ultrasonic transducer for generating ultrasonic vibrations to be propagated to said obturator; and
    a driving energy generator for generating an ultrasonic signal for driving to be supplied to said ultrasonic transducer.

16. An ultrasonic trocar system comprising:
    a cannula having a guide bore;
    an obturator to be passed through said guide bore of said cannula so that the obturator can be removed;
    a vibration generating means for generating ultrasonic vibrations to be propagated to said obturator, wherein said obturator is vibrated at an ultrasonic frequency to puncture a somatic layer and an intermediate member is interposed between said cannula and said obturator; and
    a vibration control means for providing control so that vibrational energy whose level is equal to or larger than a permissible level cannot be propagated from a portion of the distal part of said obturator in contact with a living body to the living body, wherein said vibration control means includes a constant amplitude driving means for driving said obturator at a constant amplitude, and an amplitude setting means for performing setting in such a away that when a load on said obturator increases, the value of said constant amplitude gets larger automatically, and when the load on said obturator decreases, the value of said constant amplitude gets smaller automatically.

17. An ultrasonic trocar system comprising:

a cannula having a guide bore;

an obturator to be passed through said guide bore of said cannula so that the obturator can be removed;

a vibration generating means for generating ultrasonic vibrations to be propagated to said obturator, wherein said obturator is vibrated at an ultrasonic frequency to puncture a somatic layer and an intermediate member is interposed between said cannula and said obturator; and a vibration control means for providing control so that vibrational energy whose level is equal to or larger than a permissible level cannot be propagated from a portion of the distal part of said obturator in contact with a living body to the living body, wherein said vibration control means includes a constant amplitude driving means for driving said obturator at a constant amplitude, and an amplitude varying means for continuously varying the value of said constant amplitude from any minimum value to maximum value so that a pressure load on said obturator can remain substantially constant.

18. An ultrasonic trocar system, comprising:

a cannula having a guide bore;

an obturator to be passed through said guide bore of said cannula so that the obturator can be removed;

a vibration generating means for generating ultrasonic vibrations to be propagated to said obturator, wherein said obturator is vibrated at an ultrasonic frequency to puncture a somatic layer and an intermediate member is interposed between said cannula and said obturator; and a drive unit for driving an ultrasonic transducer serving as said vibration generating means, and a switch means, connected to said drive unit, for controlling the ON or OFF state of output of ultrasonic vibrations from said ultrasonic transducer, wherein said drive unit includes:

an ultrasound output setting means for use in setting an output value of ultrasound supplied from said ultrasonic transducer; and a control means for providing control by changing the operative state of said system in such a way that when said drive unit is started by manipulating said switch means, ultrasound output from said ultrasonic transducer is set to a value larger than a given set output value to be set with said ultrasound output setting means, and that after said drive unit is started, when a predetermined given set time has elapsed, ultrasound output from said ultrasonic transducer is set to the set output value.

19. An ultrasonic trocar system according to claim 18, wherein said control means extends output control in such a way that when said drive unit is started, an amplitude becomes larger than an amplitude associated with the set output value for only a certain period of time.

20. An ultrasonic trocar system according to claim 18, wherein said control means extends output control in such a way that when said drive unit is started, an output of a maximum amplitude is provided for only a period of time associated with the set output value.

21. An ultrasonic trocar system according to claim 18, wherein said drive unit offers both a continuous vibration mode in which ultrasonic vibrations are made steadily and continuously and an intermittent vibration mode in which ultrasonic vibrations are made intermittently as operation modes, and makes it possible to set the operation modes selectively using said switch means.

* * * * *